(12) United States Patent
Maehr

(10) Patent No.: US 9,249,107 B2
(45) Date of Patent: *Feb. 2, 2016

(54) PYRIMIDINE CARBOXAMIDE DERIVATIVES

(71) Applicant: Hubert Maehr, Wayne, NJ (US)

(72) Inventor: Hubert Maehr, Wayne, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/987,972

(22) Filed: Sep. 20, 2013

(65) Prior Publication Data

US 2015/0087665 A1 Mar. 26, 2015

(51) Int. Cl.
*C07D 239/02* (2006.01)
*C07D 239/28* (2006.01)
*C07D 403/04* (2006.01)

(52) U.S. Cl.
CPC ............ *C07D 239/28* (2013.01); *C07D 403/04* (2013.01)

(58) Field of Classification Search
CPC .. A61K 31/505; C07D 239/02; C07D 239/28; C07D 403/04
See application file for complete search history.

(56) References Cited

U.S. PATENT DOCUMENTS 8,580,805 B2 * 11/2013 Maehr ........................... 514/274
2012/0053346 A1 * 3/2012 Maehr ........................... 544/316

* cited by examiner

*Primary Examiner* — Erich A Leeser

(57) ABSTRACT

The invention relates to a compound of the formula (1)

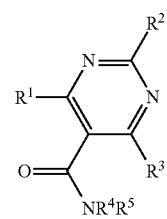

wherein the substituents are as defined herein, and a pharmaceutically acceptable salt of the compound of formula (1). The compounds of formula (1) and their salts possess inflammation inhibiting properties and are therefore useful in the treatment and prevention of conditions related to inflammations such as inflammatory joint diseases. The compounds of formula (1) are also useful for the treatment of diseases where chronic inflammation is the underlying cause. This application relates to compounds of formula (1), methods for their preparation, pharmaceutical compositions comprising these compounds, and their use for the preparation of a medicament for the treatment of humans and animals.

8 Claims, No Drawings

PYRIMIDINE CARBOXAMIDE DERIVATIVES

BACKGROUND OF THE INVENTION

1. Field of the Invention

This application relates to anti-inflammatory agents. More specifically, the invention relates to compounds of the general formula (1), methods for their preparation, medicaments comprising these compounds, and their use for the treatment of humans and animals.

2. Background

According to a report in Morbidity and Mortality Weekly Report (MMWR 2007, 56, 423), arthritis and other rheumatic conditions, e.g., gout, lupus, and fibromyalgia, affect approximately 46 million adults in the United States, resulting in substantial disability and costs of $128 billion annually. The number of U.S. adults with doctor-diagnosed arthritis has been projected to reach nearly 67 million adults by the year 2030, including 25 million adults who are expected to have arthritis-attributable activity limitations. Among 48 states, the median projected increase in doctor-diagnosed arthritis from 2005 to 2030 will be 16%; a total of 14 states are projected to have increases of 30% to 87%.

The report further states that greater use of existing evidence-based interventions and development of new interventions aimed at decreasing pain, improving function, and delaying disability associated with arthritis are needed to reduce the impact of these projected increases, particularly in those states that will be most heavily affected. These statistics, together with recent studies that suggest links between chronic inflammation and many other disorders underscore the importance of anti-inflammatory drugs. Chronic inflammation may be the mediator for many adverse conditions ranging from allergies to serious health impairments such as atherosclerosis, cancer, osteoporosis, Alzheimer's disease and immune disorders such as myopathies, often in conjunction with others, for example systemic sclerosis, and include dermatomyositis, polymyositis, and inclusion body myositis.

There are now over a 100 medications being used in the treatment of arthritis and related conditions. Over-the-counter and prescription medications are the traditional treatment option for these diseases. With every response, inevitable drug side effects and adverse reactions to a specific medication are common and vary with the individual patient. In the attempt to minimize specific side effects, patients continually change their drug regimens and this need for change is reflected by such a large drug portfolio.

3. Overview of Pertinent Science and Biological Impact

The metabolites of arachidonic acid, such as prostaglandins, lipoxygenases, and thromboxanes are produced in many tissues and play an important role not only in many physiological events, but also in pathophysiological conditions, especially inflammation and cancer (Konturek P C, et al., J Physiol Pharmacol, 2005, 56 Suppl 5, 57-73). Cyclooxygenase-2 (COX-2) is an inducible form of prostaglandine-H synthase and mediates prostaglandin synthesis during inflammation. It is also overexpressed in certain tumors and ascribed to carcinogenic events, especially colon carcinogenesis (Kawamori T, et al., Cancer Research 1998, 58, 419-412).

The embodiment relates to new compounds of formula (1) as potent inhibitors of COX-2 activity in cell based assays. Said compounds, however, show relatively weak inhibitions of isolated COX-1, COX-2, and LOX enzymes. This property indicates that compounds of formula (1) inhibit the observed prostaglandin E-2 ($PGE_2$) production in the cell-based assays of COX-2 by a mechanism that is beyond simple inhibition of the COX-2 enzyme. Although said compounds typically exhibited weaker activities than classic COX inhibitors in other COX-dependent models, they show very potent activities in the adjuvant-induced arthritis model in rats which indicates potential use for the treatment of rheumatoid arthritis and other chronic inflammatory conditions and diseases where inflammation is the underlying cause. This experimental model of polyarthritis is used widely for preclinical testing of anti-arthritic agents who are either under preclinical or clinical investigation or currently used as therapeutics in this disease (Pearson C M, Proc Soc Exp Biol Med 1956, 91, 95-100; Carlson R P, et al., Int J Immunopharmacol 1985, 7, 811; Benslay D N and Bendele A M, Agents Action 1991, 34, 254). Furthermore, the observed inhibition of COX-2-dependent $PGE_2$ synthesis by compounds of formula (1) is particularly pronounced in human rheumatic synovial cells which is considered of relevance in human rheumatoid arthritis. These properties, together with a virtual absence of gastrointestinal liabilities, set the compounds of formula (1) apart from similar molecular entities which have been described previously. Compounds of the formula (1) are expected to afford a new category of anti-inflammatory drugs with utility as chemopreventive agents in oncology, asthma, neurodegenerative diseases and heart diseases.

4. Prior Art

The compounds that are subject to this embodiment are novel and the novelty of the compounds of formula (1) is underscored by the unprecedented biological properties outlined above. The most preferred compounds of this embodiment contain three significant structural features, namely a carboxamide, a pyrimidine ring, and either a 4-hydroxy-3,5-(ditert-butyl)phenyl or a 4,6-ditert-butyl-5-hydroxy-pyrimidin-2-yl moiety. These elements are independently present in known medications, including compounds with anti-inflammatory properties, but there is no precedent that combines all three in one molecule. Some of the more related drug candidates claim ion-channel modulatory properties, others claim Syk tyrosine kinase inhibition based on in vitro studies, still others claim anti-inflammatory activity, but those claims are merely based on cellular in vitro inhibition of certain transcription factors and chemokines. Unlike our embodiment, none of them actually demonstrate unmitigated anti-inflammatory activity by the reduction of swelling in a diseased joint of a warm-blooded animal and gastrointestinal drug tolerance. The following references are examples of drug candidates that contain the structural features mentioned above:

Kadin, S B, 1985, U.S. Pat. No. 4,556,672; Ikuta, H, et al., J Med Chem 1987, 30, 1995-1998; Hammond, M L, 1988, U.S. Pat. No. 4,734,421; Connor, D T, 1992, U.S. Pat. No. 5,124,347; Unangst, P C, et al., J Med Chem 1994, 37, 322; Maehr, H, 1996, U.S. Pat. No. 5,523,310; Belliotti, T R, 1994, U.S. Pat. No. 5,356,898; Pepin, R, 1995, U.S. Pat. No. 5,475,132; Suto, M J, 1998, U.S. Pat. No. 5,811,428; Talley J J, et al., J Med Chem 2000, 43, 775-777; Bös, M, 2001, U.S. Pat. No. 6,274,588; Hisamichi, H, 2002, U.S. Pat. No. 6,432,963; Palanki, M S S, et al., Bioorg Med Chem Lett 2002, 2573-2577; Altisen, R C, 2005, US Patent Appl. Publ. 018204 A1; Waelchli, R, et al., Bioorg Med Chem Lett 2006, 16, 108-112; Martinborough, E, US Patent 2006/0160817; Sondhi, S M et al., Bioorg Med Chem 2007, 15, 3334-3344; Amir, H, et al., Indian J Pharm Sci 2007, 69, 337-343; Ohno, S, US Patent 2008/0070903; Nofal Z M, et al., Acta Pol Pharm. 2011, 68, 507-517.

BRIEF SUMMARY OF THE INVENTION

The invention relates to a compound of formula

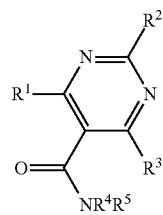

(1)

wherein $R^1$ is selected from, but not limited to, a group comprising aryl, heteroaryl or a heterocyclic group which may be substituted at substitutable positions with one or more radicals selected from the group including hydroxy, halo, cyano, nitro, amino, alkyl, aryl, heteroaryl, (cycloalkyl)alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, (aminosulfonyl)aminoalkyl, N-acylaminosulfonylalkyl, carboxyalkyl, alkoxycarbonylalkyl, aryloxycarbonylalkyl, carboxy(halo)alkyl, alkoxycarbonyl(halo)alkyl, aryloxycarbonyl(halo)alkyl, aminocarbonyl(halo)alkyl, heterocyclic (lower) alkyl, halo(lower)alkyl, lower alkenyl, arylalkenyl, lower alkylsulfanyl, lower alkylsulfinyl, lower alkylsulfonyl, arylsulfonyl, heteroarylsulfonyl, (cycloalkyl)alkylsulfonyl, aminosulfonyl, acylaminosulfonyl, aminosulfonylamino, lower alkylsulfonyloxy, acylamino, arylamino, heteroarylamino, aroylamino, lower alkyl(acyl)amino, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic)oxycarboxyl, aminocarbonyl, and

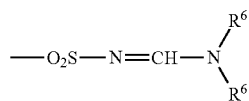

wherein $R^6$ is lower alkyl, or, taken together, may constitute a ring system as in N-piperidinyl, N-pyrrolidinyl and the like, or the ring system may contain one or more additional heteroatoms, as in N-morpholino, N-piperazinyl and the like, and wherein the ring carbon atoms may be present in the form of carbonyl groups as in 2-piperidon-1-yl;

$R^2$ is selected from, but not limited to, a group comprising aryl, heteroaryl or a heterocyclic group which may be unsubstituted or substituted at substitutable positions with one or more radicals selected from the group consisting of amino, cyano, halo, hydroxy, nitro, thio, carboxy, alkyl, deuteroalkyl, haloalkyl, alkenyl, alkoxy, alkylsulfanyl, alkylsulfinyl, alkylsulfonyl, arylsulfanyl, arylsulfinyl, arylsulfonyl, aminoalkyl, hydroxyalkyl, aminosulfonyl, aminosulfonylamino, acylaminosulfonyl, acyloxy, aroyloxy, heteroaroyloxy, acylamino, aroylamino, heteroaroylamino, alkyl(acyl)amino, alkylcarbonyl, alkoxycarbonyl, and aminocarbonyl; $R^2$ is further selected from, but not limited to, a group comprising H, halo, thio, carboxy, carbamoyl, cyano, hydroxy, alkyl, deuteroalkyl, cyanoalkyl, haloalkyl, hydroxyalkyl, alkoxyalkyl, aminoalkyl, arylalkyl, aryloxyalkyl, heteroaryloxyalkyl, alkylcarbonylalkyl, aminocarbonylalkyl, aminosulfonylalkyl, (aminosulfonyl)aminoalkyl, (acylamino)sulfonylalkyl, alkylsulfonylalkyl, carboxyalkyl, carboxy(halo)alkyl, carboxy(amino)alkyl, alkoxycarbonylalkyl, alkoxycarbonyl(halo)alkyl, alkoxycarbonyl(amino)alkyl, aminocarbonyl(halo)alkyl, aminocarbonyl(amino)alkyl, (heterocyclic)alkyl, lower alkenyl, alkoxy, deuteroalkoxy, aryloxy, alkylsulfanyl, alkylsulfinyl, alkylsulfonyl, arylsulfanyl, arylsulfinyl, arylsulfonyl, heteroarylsulfinyl, amino, aroylamino, heteroaroylamino, carboxyalkylamino, carbamoylalkylamino, alkoxycarbonylalkylamino, carboxy(amino)alkylamino, ureido, and

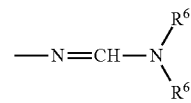

wherein $R^6$ is as defined above;

$R^3$ is H, lower alkyl, deuteroalkyl or halo(lower)alkyl;

$R^4$ is H, hydroxy, alkyl, deuteroalkyl, cyanoalkyl, haloalkyl, hydroxyalkyl, alkoxyalkyl, aminoalkyl, arylalkyl, acylalkyl, arylalkyl, lower alkenyl, lower alkoxy, deuteroalkoxy, or aryloxy, and $R^5$ is selected from, but not limited to, a group comprising H, alkyl, deuteroalkyl, (cycloalkyl)alkyl, haloalkyl, hydroxyalkyl, alkoxyalkyl, aminoalkyl, acylalkyl, arylalkyl, aroylalkyl, aryloxyalkyl, heteroaryloxy(lower) alkyl, 5- or 6-membered heterocyclic alkyl, alkenyl, aryl substituted alkenyl, alkylsulfonyl, (cycloalkyl)alkylsulfonyl, arylsulfonyl, heteroarylsulfonyl, aminosulfonyl, carboxyl, alkylcarbonyl, cycloalkylcarbonyl, alkoxycarbonyl, aminocarbonyl, arylcarbonyl, heteroarylcarbonyl, (heterocyclic)carbonyl, alkylcarbonylalkyl, alkoxycarbonylalkyl, aryloxycarbonylalkyl, heteroaryloxycarbonylalkyl, aminocarbonylalkyl, aminosulfonylalkyl, or a 5- or 6-membered heterocyclic group, (aminosulfonyl)aminoalkyl, N-acylaminosulfonylalkyl, carboxy(halo)alkyl, alkoxycarbonyl(halo)alkyl, aminoalkyl, aminocarbonyl(halo)alkyl, heterocyclic(lower) alkyl, and $R^4$ and $R^5$ taken together, may constitute a ring system that may include one or more additional heteroatoms, as in 1-piperidinyl, morpholino, 3-thiazolidinyl, 1,2,3-triazol-1-yl, and the like, and wherein the ring carbon atoms may be present in the form of carbonyl groups as in 2-piperidon-1-yl or 2,6-piperidinedion-1-yl, and a pharmaceutically acceptable salt of the compound of formula (1).

The embodiment relates to new substituted pyrimidine-5-carboxamides and pharmaceutically acceptable salts thereof. The compounds of formula (1) and their salts delineated above possess inflammation inhibiting properties and are therefore useful in the treatment and prevention of conditions related to inflammations, such as inflammatory joint diseases, or diseases where aberrant or chronic inflammation is the underlying cause.

The embodiment relates further to processes for the preparation of said substituted pyrimidine-5-carboxamides, to pharmaceutical compositions comprising the same, and to methods of using the same therapeutically in the treatment and/or prevention of various diseases, especially inflammatory conditions, various pains, collagen diseases, autoimmune diseases such as multiple sclerosis, rheumatoid arthritis, type I diabetes, inflammatory bowel disease, autoimmune thyroid disease and psoriasis, various immunity diseases and thrombosis in humans or animals, rheumatoid spondylitis, osteoarthritis, gouty arthritis, etc., inflammatory skin condition, e.g., sunburn, eczema, etc, inflammatory eye condition, e.g., conjunctivitis, etc., lung disorder in which inflammation is involved, e.g., asthma, bronchitis, pigeon fancier's disease, farmer's lung, etc, condition of the gastrointestinal tract associated with inflammation, e.g., aphthous ulcer, Crohn's disease, atropic gastritis, gastritis varialoforme, ulcerative colitis, coeliac disease, regional ileitis, irritable bowel syndrome, etc., gingivitis, inflammation, pain and tumescence after operation or injury, pain and other conditions associated with inflammation, particularly those in which LOX and COX products are a factor, diseases in which COX— and LOX-mediated metabolites play a procarcinogenic role, systemic lupus erythematosus, scleroderma, polymyositis, periarteritis nodosa, rheumatic fever, Sjögren's syndrome, Behcet disease, thyroiditis, nephrotic syndrome, aplastic anemia, myasthenia gravis, uveitis, contact dermatitis, psoriasis, Kawasaki disease, sarcoidosis, Hodgkin's disease, and the like. The object compounds are expected to be useful mainly as therapeutic and/or preventive agents for conditions where inflammation is the underlying cause. The object compounds are also expected to be useful for the treatment of cardiovascular or cerebrovascular diseases, liver disorders, and the diseases caused by hyperglycemia and hyperlipemia.

One object of the embodiment is to provide new and useful pyrimidine-5-carboxamide compounds of formula (1) and pharmaceutically acceptable salts thereof which possess anti-inflammatory, analgesic, antithrombotic and anti-oncogenetic activities.

Another object of this embodiment is to provide new and useful compounds of formula (1) and pharmaceutically acceptable salts thereof to counteract proliferation of tumor cells, especially as it pertains to various cancers, such as colon cancer.

Another object of this embodiment is to provide a novel molecular scaffold for medicinal research in the form of compounds of formula (1), with the aim to find new medicines by applying combinatorial chemistry to the substituents $R^1$, $R^2$, $R^3$, and $R^4$ in the compound of formula (1), thus extending and further optimizing the pharmacological utility of a compound of formula (1). The methods for combinatorial chemistry are well known and have been described (e.g., Maehr, H, Bioorg Med Chem 1997, 5, 473).

Another object of the embodiment is to provide processes for the preparation of a compound of formula (1) and salts thereof.

Still further object of the embodiment is to provide a therapeutic method for the treatment and/or prevention of inflammatory conditions, various pains and other diseases outlined above, which comprises administering to a mammal, preferably human, a therapeutically effective amount of a compound of formula (1).

Still further object of the embodiment is to provide therapeutically effective amounts of a compound of formula (1) in the manufacture of a medicament for the treatment of the disease conditions as outlined previously.

In another aspect, the embodiment relates to the usage of the compounds of formula (1), and their salts described above, for the treatment or prevention of inflammations and inflammation-related conditions, such as inflammatory joint disease, for example, arthritis.

In another aspect, the embodiment relates to pharmaceutical compositions which consist of a therapeutically effective amount of the compound of formula (1) or its pharmaceutically acceptable salt, together with a pharmaceutically acceptable carrier. Such compositions are preferably for the treatment of diseases outlined above.

In another aspect, the embodiment relates to pharmaceutical compositions consisting of a solution or suspension, using a pharmaceutically acceptable carrier, of a compound of formula (1) described above.

In another aspect, the embodiment relates to the administration of a compound of formula (1) in a form suitable for the enteral or parenteral administration.

In yet another aspect, the embodiment relates to a method of administering a compound of formula (1) together with delivery vehicles such as liposomes, polymersomes, and dendrimersomes, or in microencapsulated form, such as nanoparticles, or in the form of emulsions or microemulsions.

In yet another aspect, the embodiment relates to a method of use of a compound of formula (1) in combination with stabilizing agents such as antioxidants.

In accordance with the methods of the embodiment, a compound of formula (1) can be administered in combination with a pharmaceutically acceptable carrier. In advantageous embodiments, the pharmaceutically acceptable carrier provides sustained delivery of the compound of formula (1) to a subject after administration to the subject. Alternatively, controlled release can be accomplished by pegylation as known to those skilled in the art.

In accordance with the methods of the embodiment, the compound of formula (1) can be administered in combination with soluble macromolecular entities, such as cyclodextrin and suitable derivatives thereof, or polyethylene glycol-containing polymers, in order to improve their solubility, dissolution rate, taste-masking, bioavailability and/or stability for use in any of the aforementioned modes of administration. Drug-cyclodextrin complexes, for example, are found to be generally useful for many dosage forms and administration routes. Both inclusion and non-inclusion complexes may be used. As an alternative to direct complexation with the drug, the cyclodextrin may be used as an auxiliary additive, i.e., as a carrier, diluent, or solubiliser. Most commonly used for these purposes are alpha-, beta- and gamma-cyclodextrins, examples of which may be found in WO 91/11172, WO 94/02518 and WO 98/55148.

In accordance with the methods of the invention, a compound of formula (1) can be administered in various concentrations. The dosages may vary depending on the particular indication, route of administration, and subject. Generally, said compound is administered at a concentration of about 1 mg to about 30 mg/kg of body weight.

In yet another aspect, the embodiment relates to the use of a compound of formula (1) in combination with other drugs that can augment the desired effect in a diseased subject.

In accordance with this embodiment, the treatment can be extended to viral infections by using a composition comprising an effective amount of a compound of formula (1), a local anesthetic, and an antiviral drug.

In accordance with this embodiment the topical composition comprises an effective amount of a compound of formula (1), a local anesthetic such a benzocaine or lidocaine, and an antiviral drug, such as acyclovir, peniclovir, ganciclovir, a prodrug thereof, and a combination thereof. The prodrug of the acyclovir comprises valacyclovir, and the prodrug of the penciclovir comprises famciclovir. The preparation of a formulation, comprising all ingredients in the form of a suitable gel or cream, is known to those skilled in the art.

In accordance with this embodiment, the effective amount of the compound of formula (1), the local anesthetic, or the antiviral drug can vary, typically between 1-40 weight percent.

In another aspect, the embodiment provides a packaged formulation which includes a pharmaceutical composition, comprising a compound of formula (1) and a pharmaceutically acceptable carrier, packaged with instructions for use in the treatment and prevention of conditions as outlined above.

In yet another aspect, the embodiment relates to processes for preparing a compound of the formula

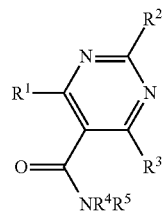

(1)

wherein the substituents $R^1$, $R^2$, $R^3$, $R^4$, and $R^5$ are as described above. The method consist of reacting a compound of formula

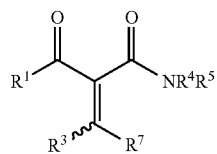

(2)

wherein $R^1$, $R^3$, $R^4$ and $R^5$, are as defined above, and $R^7$ is selected from dialkylamino, 1-pyrrolidinyl, 1-piperidinyl, alkoxy, phenoxy, anilino, hydroxy, and the like, in a cyclocondensation with an amidine of the formula $HN=C(R^2)NH_2$ wherein $R^2$ has been defined previously. These amidines are usually employed as their salt in polar solvents together with suitable bases. Such transformations are closely related to cyclocondensations of amidines with dicarbonyl compounds, which have been known for a long time (Evans, P N, J Pract Chem 1892, 46, 352, and 1893, 48, 489) and further elaborated (Schenone, P, et al., J Heterocycl Chem 1982, 19, 135, and 1990, 27, 295).

In yet another aspect, the embodiment relates to processes for preparing a compound of the formula (2). The method consists of a reaction of compound of the formula

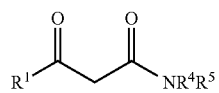

(3)

wherein the substituents $R^1$, $R^4$ and $R^5$ are as defined above, with an N,N-dialkylalkanamide dialkyl acetal, such as N,N-dimethylformamide dialkyl acetal, or 1-pyrrolidinecarboxaldehyde dialkyl acetal, 1-piperidinecarboxaldehyde dialkyl acetal, N,N-dimethylacetamide dialkyl acetal, N,N-dimethylpropionamide dialkyl acetal and the like, or with a suitable carboxylic acid derivative such as an orthoester, an acid anhydride, or an activated ester, and the like. Similar alkylidenation reactions of dicarbonyl compounds as substrates are referenced above.

In yet another aspect, the embodiment relates to a process for preparing a compound of the formula (3). The method consist of reacting a compound of formula

(4)

wherein $R^1$ is as defined above, with a suitable acyl transfer agent such as dimethyl carbonate, diphenylcarbonate, an activated carboxylic acid derivative, such as an as a carboxylic acid anhydride, an alkyloxycarbonyl chloride or a suitable imidazoyl-1-carbonyl compound, to form a compound of the formula (3a) wherein the substituent R is lower alkoxy, haloalkoxy, phenoxy, 1-imidazoyl, or the like. These reactions are essentially Claisen reactions and well known to the practitioners. The conversion of the compound of formula (3a), wherein R is alkoxy, to the carboxamide of formula (3) can be achieved by direct aminolysis or through the intermediacy of a hydrolytic step and rebuilding the carboxamide function from the carboxylic acid of the formula (3b), by methods known to those skilled in the art.

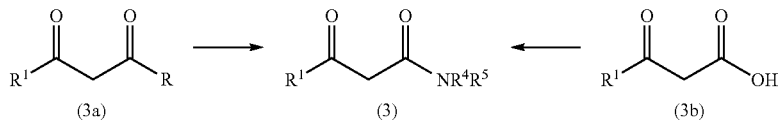

In the aspect delineated above, the embodiment relates to a process of producing the preferred compound of the formula

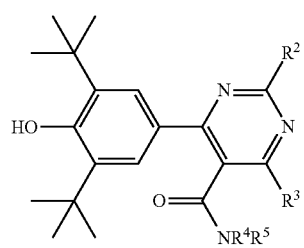

(1a)

wherein the substituent $R^2$, $R^3$, $R^4$, and $R^5$ are as defined previously. The method consists of a cyclocondensation of a compound of formula

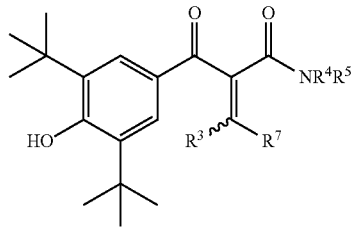

(2a)

wherein the substituents $R^3$, $R^4$, $R^5$, and $R^7$ are as defined previously, with a carbamimidoyl compound as described above.

In yet another aspect, the embodiment relates to a method of synthesis of a compound of formula (2a) which consists of subjecting a compound of the formula

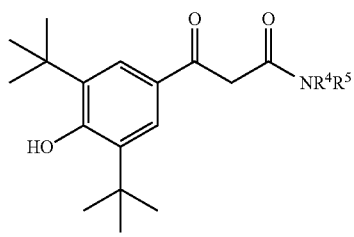

(3c)

wherein the substituents $R^4$ and $R^5$ are as defined above, to an alkylidination reaction as delineated above.

In yet another aspect, the embodiment relates to a method of synthesis of a compound of formula (3c) which consists of subjecting a compound such as

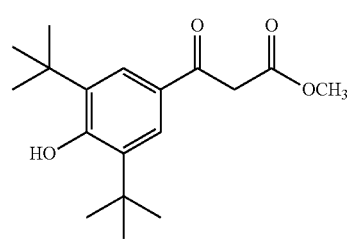

(3d)

to aminolysis conditions using an amine of the formula $NHR^4R^5$, wherein the substituents $R^4$ and $R^5$ are as defined above.

In yet another aspect, the embodiment relates to a method of synthesis of a compound of formula (3d) which consists of subjecting a compound of the formula

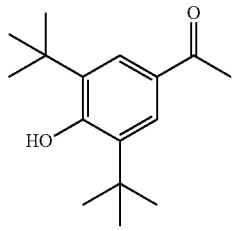

(4a)

to a Claisen-type reaction with dimethylcarbonate together with 3 equivalents of a strong base such as lithium bis(trimethylsilyl)amide in a nonprotic, polar solvent such as tetrahydrofuran, followed by neutralization and extractive isolation.

In yet another aspect, the embodiment relates to an alternate process for preparing a compound of the formula (1a) which consists of subjecting a compound of the formula

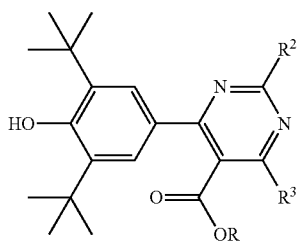

(1b)

wherein the substituents $R^2$ and $R^3$ are as defined previously and R is lower alkyl, haloalkyl, or aryl, to aminolysis conditions using a suitable amine of the formula $NHR^4R^5$.

Alternatively, the compound of the formula (1a) can be prepared in a two-step process by hydrolyzing the ester function in the compound of the formula (1b) and rebuilding the amide group from the resulting carboxylic acid level using methods commonly applied in peptide synthesis and known to those skilled in the art.

In yet another aspect, the embodiment relates to a method of synthesis of a compound of formula (1) wherein $R^1$ is 5-hydroxy-4,6-ditert-butyl-pyrimidin-2-yl. The synthetic steps consist of the conversion of the previously disclosed methyl ester of formula (5) to the ketone of formula (4b) by known methods and exemplified in numerous publications such as Sato, T, et al., Tetrahedron Lett. 1986, 27, 4339; Sato, T, et al., J Org Chem 1988, 53, 1207; Huet, F, et al., Tetrahedron 1973, 29, 479-485; Bestmann, H J, Chem Ber 1962, 95, 1513-1527.

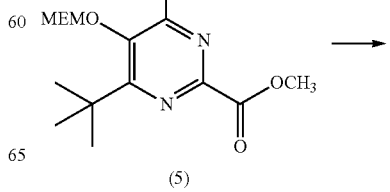

(5)

-continued

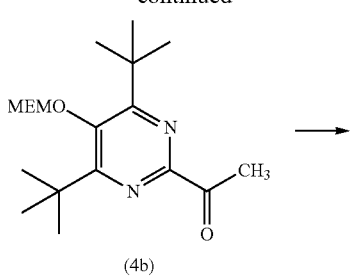

(4b)

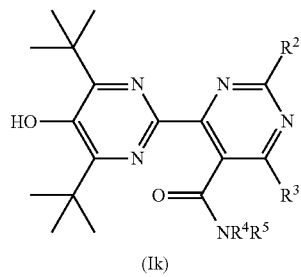

(Ik)

The compound of formula (5) was described by Belliotti T R et al., 1994, U.S. Pat. No. 5,356,898 as previously quoted. The subsequent protocol for the conversion of the compound (4b) to a compound of formula (1k) can proceed in analogy to the syntheses of the compound of formula (1) wherein $R^1$ is 4-hydroxy-3,5-ditert-butyl-phenyl as outlined above as described in detail below.

DETAILED DESCRIPTION OF THE INVENTION

The invention relates to a compound of the formula

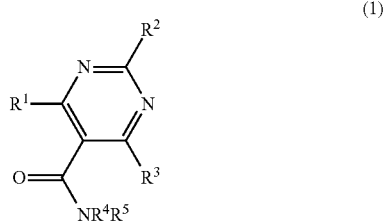

(1)

wherein $R^1$ is selected from, but not limited to, a group comprising aryl, heteroaryl or a heterocyclic group which may be substituted at substitutable positions with one or more radicals selected from the group including hydroxy, halo, cyano, nitro, amino, alkyl, aryl, heteroaryl, (cycloalkyl) alkyl, cyanoalkyl, deuteroalkyl, haloalkyl, hydroxyalkyl, aminoalkyl, alkoxyalkyl, arylalkyl, aryloxyalkyl, alkylcarbonylalkyl, aminocarbonylalkyl, aminosulfonylalkyl, (aminosulfonyl)aminoalkyl, N-acylaminosulfonylalkyl, carboxyalkyl, alkoxycarbonylalkyl, aryloxycarbonylalkyl, carboxy(halo)alkyl, alkoxycarbonyl(halo)alkyl, aryloxycarbonyl(halo)alkyl, aminocarbonyl(halo)alkyl, heterocyclic (lower)alkyl, halo(lower)alkyl, lower alkenyl, arylalkenyl, lower alkylsulfanyl, lower alkylsulfinyl, lower alkylsulfonyl, arylsulfonyl, heteroarylsulfonyl, (cycloalkyl)alkylsulfonyl, aminosulfonyl, acylaminosulfonyl, aminosulfonylamino, lower alkylsulfonyloxy, acylamino, arylamino, heteroarylamino, aroylamino, lower alkyl(acyl)amino, carboxy, alkoxy, haloalkoxy, deuteroalkoxy, acyloxy, aryloxy, heteroaryloxy, alkylcarbonyl, arylcarbonyl, heteroarylcarbonyl, (heterocyclic)carbonyl, arylalkylcarbonyl, alkoxycarbonyl, aryloxycarbonyl, (heterocyclic)oxycarboxyl, aminocarbonyl, and

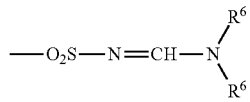

wherein $R^6$ is lower alkyl, or, taken together, may constitute a ring system as in N-piperidinyl, N-pyrrolidinyl and the like, or the ring system may contain one or more additional heteroatoms, as in N-morpholino, N-piperazinyl and the like, and wherein the ring carbon atoms may be present in the form of carbonyl groups as in 2-piperidon-1-yl;

$R^2$ is selected from, but not limited to, a group comprising aryl, heteroaryl or a heterocyclic group which may be unsubstituted or substituted at substitutable positions with one or more radicals selected from the group consisting of amino, cyano, halo, hydroxy, nitro, carboxy, alkyl, deuteroalkyl, haloalkyl, alkenyl, alkoxy, alkylsulfanyl, alkylsulfinyl, alkylsulfonyl, arylsulfanyl, arylsulfinyl, arylsulfonyl, aminoalkyl, hydroxyalkyl, aminosulfonyl, aminosulfonylamino, acylaminosulfonyl, acyloxy, aroyloxy, heteroaroyloxy, acylamino, aroylamino, heteroaroylamino, alkyl(acyl)amino, alkylcarbonyl, alkoxycarbonyl, and aminocarbonyl; $R^2$ is further selected from, but not limited to, a group comprising H, amino, halo, thio, carboxy, carbamoyl, cyano, hydroxy, alkyl, deuteroalkyl, cyanoalkyl, haloalkyl, hydroxyalkyl, alkoxyalkyl, aminoalkyl, arylalkyl, aryloxyalkyl, heteroaryloxyalkyl, alkylcarbonylalkyl, aminocarbonylalkyl, aminosulfonylalkyl, (aminosulfonyl)aminoalkyl, (acylamino)sulfonylalkyl, alkylsulfonylalkyl, carboxyalkyl, carboxy(halo)alkyl, carboxy(amino)alkyl, alkoxycarbonylalkyl, alkoxycarbonyl (halo)alkyl, alkoxycarbonyl(amino)alkyl, aminocarbonyl (halo)alkyl, aminocarbonyl(amino)alkyl, (heterocyclic) alkyl, lower alkenyl, alkoxy, deuteroalkoxy, aryloxy, alkylsulfanyl, alkylsulfinyl, alkylsulfonyl, arylsulfanyl, arylsulfinyl, arylsulfonyl, heteroarylsulfinyl, amino, aroylamino, heteroaroylamino, carboxyalkylamino, carbamoylalkylamino, alkoxycarbonylalkylamino, carboxy(amino) alkylamino, ureido, and

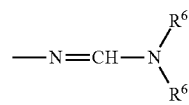

wherein $R^6$ is as defined above;

$R^3$ is H, lower alkyl, deuteroalkyl or halo(lower)alkyl;

$R^4$ is H, hydroxy, alkyl, deuteroalkyl, cyanoalkyl, haloalkyl, hydroxyalkyl, alkoxyalkyl, amino alkyl, aryl alkyl, acylalkyl, arylalkyl, lower alkenyl, lower alkoxy, deuteroalkoxy, or aryloxy, and $R^5$ is selected from, but not limited to, a group comprising H, alkyl, deuteroalkyl, (cycloalkyl)alkyl, haloalkyl, hydroxyalkyl, alkoxyalkyl, aminoalkyl, acylalkyl, arylalkyl, aroylalkyl, aryloxyalkyl, heteroaryloxy(lower)alkyl, 5- or 6-membered heterocyclic alkyl, alkenyl, aryl substituted alkenyl, alkylsulfonyl, (cycloalkyl)alkylsulfonyl, arylsulfonyl, heteroarylsulfonyl, aminosulfonyl, carboxyl, alkylcarbonyl, cycloalkylcarbonyl, alkoxycarbonyl, aminocarbonyl, arylcarbonyl, heteroarylcarbonyl, (heterocyclic) carbonyl, alkylcarbonylalkyl, alkoxycarbonylalkyl, aryloxycarbonylalkyl, heteroaryloxycarbonylalkyl, aminocarbonylalkyl, aminosulfonylalkyl, or a 5- or 6-membered heterocyclic group, (aminosulfonyl)aminoalkyl, N-acylaminosulfonylalkyl, carboxyhaloalkyl, alkoxycarbonylhaloalkyl, aminoalkyl, aminocarbonyl(halo)alkyl, heterocyclic(lower)alkyl, and $R^4$ and $R^5$ taken together, may constitute a ring system that may include one or more additional heteroatoms, as in 1-piperidinyl, morpholino, 3-thiazolidinyl, 1,2,3-triazol-1-yl, and the like, and wherein the ring carbon atoms may be present in the form of carbonyl groups as in 2-piperidon-1-yl or 2,6-piperidinedion-1-yl, and a pharmaceutically acceptable salt of the compound of formula (1).

In the above and subsequent description of the present specification, suitable examples of the various definitions to be included within the scope of the invention are explained in detail below.

As used herein, the term "halo" means fluoro, chloro, bromo, or iodo, preferably fluoro or chloro.

The term "amino" denotes an amino group that may be unsubstituted or it may have the from of $NR^3R^4$ as described above, as in 4-pyridinylamino, anilino, morpholino, diphenylamino and N-methyl-(1H-indol-3-yl)amino for example, of which methylamino is preferred.

Suitable "aryl" may be an aromatic moiety such as phenyl, naphthyl, and the like, of which phenyl is preferable. The term "aryl" also denotes an unsubstituted or substituted aryl group wherein the substituents are chosen from, but not limited to those defined previously for $R^2$, of which 3,5-ditert-butyl-4-hydroxyphenyl and 3,5-di-methoxy-4-hydroxyphenyl are preferred.

The term "alkyl" denotes methyl, or a $C_2$-$C_{12}$ straight, saturated hydrocarbon moiety, such as ethyl, n-propyl, n-butyl, and the like, or an alkyl substituted alkyl in the form of a branched hydrocarbon chain as in isopropyl, neopentyl and the like; of these, methyl and tert-butyl are preferred. The term also includes cycloalkyl in the form of a saturated carbocycle containing 3 to 6 carbon atoms, such cyclopropyl, cyclobutyl, and cyclohexyl, for example, of which cyclopropyl is preferred.

The term "(cycloalkyl)alkyl" denotes a cycloalkyl substituted alkyl as in (cyclopropyl)methyl and (cyclohexyl)ethyl; of these, (cyclopropyl)methyl is preferred.

The term "lower" is intended to mean an alkyl chain having 1 to 6 carbon atoms.

The term "deuteroalkyl" denotes a partially or fully deuterated methyl, such as trideuteromethyl, or a lower alky, substituted with one or more deuterium atoms, such as 2,2,2-trideuteroethyl, pentadeuteroethyl and the like, of which trideuteromethyl is preferred.

The term "hydroxyalkyl" denotes a hydroxy substituted alkyl such as a hydroxymethyl group or an alkyl substituted with one or more hydroxy groups, including, but not limited to 1-hydroxyethyl, 2,3-dihydroxypropyl, and the like.

Suitable "haloalkyl" are halo-substituted alkyls and may be chloromethyl, fluoromethyl, difluoromethyl, trifluoromethyl, 2-fluoroethyl, 4-chlorobutyl, and the like, of which trifluoromethyl is preferred.

The term "arylalkyl" is an aryl substituted alkyl and includes an alkyl substituted by one or more aryl groups, such as a benzyl, phenethyl, 2-(3-fluorophenyl)ethyl, 2,2-diphenylethyl, and the like.

The term "amino" denotes an amino group that may be unsubstituted or it may have the from of $NR^4R^5$ as described above, as in 4-pyridinylamino, anilino, morpholino, diphenylamino and N-alkyl-1H-indol-3-amino, or example; of these, methylamino is preferred.

The term "aminoalkyl" is an alkyl substituted with an amino group as defined above, or an alkyl moiety substituted with one or more amino groups as defined above, such as methylaminomethyl, methylaminoethyl, ethylaminopropyl, ethylaminohexyl, N,N-dimethylaminoethyl, N,N-dimethylaminopropyl, N,N-diethylaminopropyl, 2,3-diaminopropyl, and the like.

The term "alkoxyalkyl" denotes an alkoxy substituted alkyl, such as a methoxymethyl and 3-methoxyprop-1-yl, or an alkyl radical substituted with one or more alkoxy residues as in 3,5-dimethoxy-hex-1-yl, and the like.

The term "acylalkyl" is an alkylcarbonylalkyl group, and denotes an alkyl group, including a methyl group, that is substituted with an oxoalkyl radical as in 2-oxo-1-butyl, 3-oxo-1-hexyl, and the like.

The term "alkylsulfonylalkyl" denotes an alkyl group, including a methyl group, substituted with an alkylsulfonyl group, as in (methylsulfonyl)methyl or 3-(ethylsulfonyl)-1-propyl.

The term "alkoxycarbonylalkyl" denotes an alkyl substituted with an alkoxycarbonyl residue.

The term "alkoxycarbonyl(amino)alkyl" is an alkyl substituted with an alkoxycarbonyl and an amino group.

The term "alkoxycarbonyl(halo)alkyl" is an alkyl substituted with an alkoxycarbonyl and a halo substituent.

The term "aminocarbonylalkyl" denotes an alkyl substituted with a carbamoyl group whose nitrogen atom may be unsubstituted or it may take the form of $NR^4R^5$ as defined previously, as in 6-dimethylamino-6-oxo-hexyl, or 3-amino-3-oxo-prop-1-yl, for example.

The term "aminosulfonylalkyl" denotes an alky moiety, including a methyl group, substituted with an aminosulfonyl group as in N,N-dimethylaminosulfonylmethyl, and the like.

The term "aminocarbonyl(halo)alky" is an alkyl substituted with carbamoyl and a halo substituent.

The term "ureido" means a carbamoylamino group.

The term "aminocarbonyl(amino)alkyl is an alkyl substituted with a carbamoylamino group, as in 2-ureidoethyl.

The term "aryloxyalkyl" or "aryloxy substituted alkyl" denotes an alkyl moiety substituted by one or more aryloxy residue wherein the aryl groups are unsubstituted or substituted and wherein the substituents are as described above, such as phenoxymethyl or 2-[(1-methyl-4-piperidyl)oxy]ethyl, and the like.

The term "carboxy(halo)alkyl" denotes an alkyl substituted with one or more carboxy and halo substituents.

The term "(heterocyclic)alkyl" denotes an alkyl group substituted with a heterocyclic group, as in (2-pyridyl)methyl or bis(4-pyridyl)methyl, for example.

The term "carboxy(amino)alkyl" denotes an alkyl group, including a methyl group, that is substituted with one or more carboxy and amino radicals, as in 2-carboxy-2-amino-ethyl, and the like.

The term "aminosulfonylamino" means a sulfamoylamino group.

The term "(aminosulfonyl)aminoalkyl" denotes an alky moiety substituted with an aminosulfonylamino group, as in (sulfamoylamino)methyl, and the like.

The term "aroyl" denotes a carbonyl group attached to an aryl moiety, such as benzoyl, 2-naphthoyl, and the like Suitable "aroylamino" constitute amino groups substituted with aroyl, such as benzoylamino, and the like.

The term "heteroaroylamino" denotes an amino group substituted with a heteroaroyl moiety, such as 1H-indole-3-carboxamido.

The term "carboxyalkylamino" denotes an amino group substituted with a carboxyalkyl group as in 2-(carboxyethyl)amino, (cyclopropylmethyl)amino, and the like.

The term "carbamoylalkylamino" denotes an amino group substituted with a carbamoylalkyl group, as in (carbamoylmethyl)amino, and the like.

The term "alkoxycarbonylalkylamino" denotes an amino group substituted with an alkoxycarbonylalkyl as in ((methoxycarbonyl)methyl)amino, for example.

The term "carboxy(amino)alkylamino" denotes an amino group bearing a carboxy(amino)alkyl group as defined above, as in ((2-carboxy-2-amino)ethyl)amino, for example.

The term "alkyl(acyl)amino" denotes an amino group as defined above, wherein the amino group is substituted with an alkyl and an acyl group, as in acetyl(methyl)amino, and the like.

The term "aminosulfonylamino" denotes a sulfamide group synonymous with sulfamoylamino.

The term "alkenyl" denotes a unsaturated alkyl, such as ethenyl, 1-propenyl, 2-propenyl, 1-butenyl, 2-butenyl, and the like.

The term "lower alkenyl" denotes a $C_2$-$C_6$ alkenyl.

The term "arylalkenyl" means aryl substituted alkenyl, which is an alkenyl substituted by one or more aryl groups, such as styryl, cinnamyl, 2-(4-acetylphenyl)ethenyl, and the like.

Suitable "alkoxy" may be methoxy, ethoxy, propoxy, isopropoxy, butoxy, isobutoxy, tert-butoxy and the like, in which the preferable one is methoxy; the term also includes carbocyclic alkoxy such as cyclohexyloxy.

The term "deuteroalkoxy" denotes a lower alkoxy residue wherein some, or all of the hydrogen atoms are replaced by deuterium, as in trideuteromethoxy or pentadeuteroethoxy.

The term "haloalkoxy" means a halo-substituted alkoxy including, but not limited to, 2-fluoroethoxy, 2,2-difluoroethoxy, 2,2,2-trichloroethoxy, 3-fluoropropoxy, 4-fluorobutoxy, and the like. Of these, trifluoromethoxy and 2,2,2-trifluoroethoxy are preferred.

The term "acyloxy" denotes an acyl group linked to oxygen, as in acetoxy, for example.

The term "aryloxy" denotes an aryl residue linked to oxygen, such as phenoxy.

The term "heteroaryloxy" denotes a heteroaryl residue linked to oxygen, such as 2-furyloxy.

The term "aroyloxy" denotes an aroyl group linked to oxygen, as in benzoyloxy, for example.

The term "arylcarbonyl" denotes a carbonyl group substituted by an aryl group, such as 2-fluorobenzoyl, and the like.

The term "alkylcarbonyl" means "acyl and alkanoyl" and includes cycloalkylcarbonyl, and denotes a carbonyl group substituted by an alkyl moiety, for example formyl, acetyl, propionyl, secondary butyryl, or a cycloalkyl moiety containing 3 to 6 carbon atoms, such as cyclopropylcarbonyl or cyclobutylcarbonyl.

Suitable "heterocycliccarbonyl" include "heteroarylcarbonyl" such as pyrrolidinylcarbonyl, imidazolidinylcarbonyl, piperidinocarbonyl, nicotinoyl, piperazinylcarbonyl, N-methylpiperazinylcarbonyl, or the like, in which the preferable one is pyrrolidinylcarbonyl and N-methylpiperazinylcarbonyl.

The term "alkoxycarbonyl" means a carbonyl group substituted with an alkoxy group as defined previously, for example methoxycarbonyl.

The term "aryloxycarbonyl" means a carbonyl group substituted with an aryloxy group as defined previously, for example phenoxycarbonyl.

The term "arylalkylcarbonyl" denotes a carbonyl group bearing an arylalkyl moiety as in benzyloxycarbonyl, phenethyloxycarbonyl, and the like.

The term "(heterocyclic)oxycarbonyl" means a carbonyl group substituted with a heterocyclic group via an oxygen linkage as in ((2-(pyridinyl)oxy)carbonyl.

The term "aminocarbonyl" denotes a carbamoyl group whose amino group may be unsubstituted or it may be of the form as defined in $NR^3R^4$, such as morpholinocarbonyl, for example.

The term "aminosulfonyl" denotes a sulfonyl bearing an amino group, defined previously as in $NR^5R^6$, for example, methylaminosulfonyl, ethylaminosulfonyl, dimethylaminosulfonyl, diethylaminosulfonyl, and the like.

Suitable "alkylsulfonyl" may be methylsulfonyl, ethylsulfonyl, propylsulfonyl and the like, in which the preferable one is methylsulfonyl.

Suitable "(cycloalkyl)alkylsulfonyl" are cyclopropylmethylsulfonyl and cyclohexylmethylsulfonyl.

The term "arylsulfonyl" denotes a sulfonyl group substituted with aryl, such as phenylsulfonyl, and the like.

The term "heteroarylsulfonyl" denotes a sulfonyl group substituted with heteroaryl, such as (2-pyridyl)sulfonyl, and the like.

Suitable "alkylsulfinyl" may be methylsulfinyl, ethylsulfinyl, propylsulfinyl and the like, of which the preferable one is methylsulfinyl.

Suitable "alkylsulfanyl" include methylsulfanyl and ethylsulfanyl, of which methylsulfanyl is preferred.

The term "acylaminosulfonyl" denotes an N-acylsulfamoyl group as in 2-(acetylsulfamoyl).

Suitable "acylaminosulfonylalkyl" include (acetylsulfamoyl)methyl and 2-(acetylsulfamoyl)ethyl.

The term ""heterocyclic group" includes "heteroaryl" and may include saturated or unsaturated, monocyclic or polycyclic groups containing at least one hetero atom such as nitrogen, oxygen or sulfur. The preferred examples of thus defined "heterocyclic group" may be unsaturated, 3 to 8-membered, more preferably 5 or 6-membered heteromonocyclic group containing 1 to 4 nitrogen atoms, for example, pyrrolyl, imidazolyl, pyrazolyl, pyridyl, pyridyl N-oxide, dihydropyridyl, tetrahydropyridyl, pyrimidyl, pyrazinyl, pyridazinyl, triazinyl, triazolyl, tetrazinyl, tetrazolyl, etc.; or saturated, 3 to 8-membered, more preferably 5 or 6-membered, heteromonocyclic group containing 1 to 4 nitrogen atoms, for example, pyrrolidinyl, imidazolidinyl, piperidino, piperazinyl, etc.; or unsaturated, condensed heterocyclic group containing 1 to 5 nitrogen atoms, for example, indolyl, isoindolyl, indolizinyl, benzimidazolyl, quinolinyl, isoquinolinyl, indazolyl, benzotriazolyl, etc.; or unsaturated, 3 to 8-membered heteromonocyclic group containing 1 to 2 oxygen atoms, and 1 to 3 nitrogen atoms, for example, oxazolyl, isoxazolyl, oxadiazolyl, etc.; or saturated, 3 to 8-membered heteromonocyclic group containing 1 to 2 oxygen atoms and 1 to 3 nitrogen atoms, for example, morpholino, sydnonyl, etc.; or unsaturated, condensed heterocyclic group containing 1 to 2 oxygen atoms and 1 to 3 nitrogen atoms, for example, benzoxazolyl, benzoxadiazolyl and the like, or unsaturated, 3 to 8-membered heteromonocyclic group containing 1 to 2 sulfur atoms and 1 to 3 nitrogen atoms, for example, thiazolyl, isothiazolyl, thiadiazolyl, etc.; or unsaturated, 3 to 8-membered heteromonocyclic group containing 1 to 2 sulfur atoms, for example, thienyl, etc.; or unsaturated condensed heterocyclic group containing 1 to 2 sulfur atoms and 1 to 3 nitrogen atoms, for example, benzothiazolyl, benzothiadiazolyl, etc.; or unsaturated, 3 to 8-membered heteromonocyclic group containing an oxygen atom, for example, furyl, etc.; or unsaturated, condensed heterocyclic group containing 1 to 2 sulfur atoms, for example, benzothienyl, etc.; or unsaturated, condensed heterocyclic group containing 1 to 2 oxygen atoms, for example, benzofuranyl, and the like. Of these, 4-hydroxy-3-indolyl, 6-methoxy-4-quinolinyl, and 4,6-ditert-butyl-5-hydroxy-pyrimidine-2-yl are preferred.

Suitable pharmaceutically acceptable salts of the object compound (I), containing molecular groups with basic or acidic character, are conventional non-toxic salts and include acid addition salt, for example an inorganic acid addition salt such as hydrochloride, hydrobromide, sulfate, phosphate, etc., an organic acid addition salt such as acetate, trifluoroacetate, maleate, tartrate, methanesulfonate, benzenesulfonate, toluenesulfonate, etc., a salt with an amino acid such as arginine salt, aspartic acid salt, glutamic acid salt, etc., a metal salt such as an alkali metal salt, for example a sodium salt, potassium salt, etc., and an alkaline earth metal salt such as a calcium or a magnesium salt, etc., an ammonium salt, an organic base addition salt such as trimethylamine salt, and the like.

The term "effective amount" includes an amount effective, at dosages and for periods of time necessary, to achieve the desired result, e.g., an anti-inflammatory response, for example the reduction of swelling of a joint. An effective amount of a compound of formula (1) may vary according to factors such as the disease state, age, and weight of the subject, and the ability of the compound of formula (1) to elicit a desired response in the subject. Dosage regimens may be adjusted to provide the optimum therapeutic response. An effective amount is also one in which any adverse or undesirable side effects are outweighed by the therapeutically beneficial effects.

The term "therapeutically effective amount" describes the amount of a compound of formula (1) to elicit a desirable effect and may range from about 1 to 30 mg/kg body weight, preferably between about 2 to 10 mg/kg body weight. The actual dose and the duration of treatment will be a function of the mode of administration of the drug and the nature of the subject, such as the severity of the disease or disorder, previous treatments, the general health and/or age of the subject, and other diseases present. Moreover, treatment of a subject with a therapeutically effective amount of a compound of formula (1) can include a single treatment or, preferably, can include a series of treatments. In one example, a subject is treated daily with a compound of formula (1) for a two week period using a drug concentration of 5 mg/kg body for each administration. It will also be appreciated that the effective dosage of a compound of formula (1) that is used for treatment may increase or decrease over the course of a particular treatment period.

Examples of pharmaceutically acceptable stabilizers and antioxidants include water soluble antioxidants, such as ascorbic acid, cysteine hydrochloride, sodium metabisulfite, sodium sulfite and the like, oil-soluble antioxidants, such as ascorbyl palmitate, butylated hydroxyanisole (BHA), butylated hydroxytoluene (BHT), lecithin, propyl gallate, alpha-tocopherol, and the like, and metal chelating agents, such as citric acid, ethylenediamine tetraacetic acid (EDTA), sorbitol, tartaric acid, phosphoric acid, and the like.

Compositions of the embodiment suitable for oral administration of an effective amount may be in the form of capsules, cachets, pills, tablets, lozenges with a flavored basis such as sucrose and acacia or tragacanth, powders, granules, or as a solution, suspension, or emulsion in an aqueous or non-aqueous liquid, or as an oil-in-water or water-in-oil liquid emulsion, or as an elixir or syrup, or as pastilles using an inert base, such as gelatin and glycerin, or sucrose and acacia, each containing a predetermined amount of a compound of formula (1) as an active ingredient. A compound of formula (1) may also be administered as a bolus, electuary or paste. Most preferred is the administration of the compound of formula (1) in micronized form together with an inert carrier or dispersing agent and enclosed in a gelatin capsule.

Pharmaceutical compositions of the embodiment, suitable for parenteral administration of a therapeutically effective amount, comprise a compound of formula (1) as a pharmaceutically acceptable sterile isotonic aqueous or nonaqueous solutions, dispersions, suspensions or emulsions, or as sterile powder which may be reconstituted into sterile injectable solutions or dispersions just prior to use, which may contain antioxidants, buffers, bacteriostats, or solutes which render the formulation isotonic with the blood of the intended recipient, or suspending or thickening agents.

Pharmaceutical compositions of this embodiment suitable for parenteral administration of a therapeutically effective amount can be made by forming microencapsule matrices of the compound in biodegradable polymers such as polylactide-polyglycolide. Depending on the ratio of drug to polymer, and the nature of the particular polymer employed, the rate of drug release can be controlled. Examples of other biodegradable polymers include polyorthoesters and polyanhydrides. Depot injectable formulations are also prepared by entrapping the drug in liposomes or microemulsions which are compatible with body tissue.

Examples of suitable aqueous and nonaqueous carriers which may be employed in the pharmaceutical compositions of the invention include water, ethanol, polyols such as glycerol, propylene glycol, polyethylene glycol, and the like, and suitable mixtures thereof including Mygliol®, vegetable oils, such as olive oil, and injectable organic esters, such as ethyl oleate. Proper fluidity can be maintained, for example, by the use of coating materials, such as lecithin, by the maintenance of the required particle size in the case of dispersions, and by the use of surfactants.

These compositions may also contain adjuvants such as preservatives, wetting agents, emulsifying agents and dispersing agents. Prevention of the action of microorganisms may be ensured by the inclusion of various antibacterial and antifungal agents, for example, paraben, chlorobutanol, phenol, sorbic acid, and the like. It may also be desirable to include isotonic agents, such as sugars, sodium chloride, and the like, into the compositions. In addition, prolonged absorption of the injectable pharmaceutical form may be brought about by the inclusion of agents which delay absorption such as aluminum monostearate and gelatin.

To prolong the effect of a drug, it may be desirable to slow the absorption of the drug from subcutaneous or intramuscular injection. This may be accomplished by the use of a liquid suspension of crystalline or amorphous material having poor water solubility. The rate of absorption of the drug then depends upon its rate of dissolution which, in turn, may depend upon crystal size and crystalline form and particle size in general. Alternatively, delayed absorption of a parenterally administered drug form is accomplished by dissolving or suspending the drug in an oil vehicle, for example Mygliol.

When a compound s of formula (1) is administered as a pharmaceutical to humans and animals, it can be given per se or as a pharmaceutical composition containing, for example 5 to 95% of said compound in combination with a pharmaceutically acceptable carrier.

Regardless of the route of administration selected, the compounds of the formula (1), which are used in suitable physical forms, are formulated into pharmaceutically acceptable dosage forms by conventional methods known to those skilled in the art.

According to a preferred embodiment, in the compound of formula

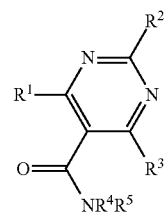

(1)

R¹ is 3,5-dimethoxy-4-hydroxyphenyl, 3-methoxy-4-hydroxyphenyl, 3,5-ditert-butyl-4-hydroxyphenyl, 4,6-ditert-butyl-5-hydroxy-pyrimidin-2-yl, and 3-indolyl, most preferably 3,5-ditert-butyl-4-hydroxyphenyl;

R² is H, alkyl, alkoxy or amino, most preferably methyl;

R³ is H or methyl, most preferably H;

R⁴ is H, methyl, trideuteromethyl, ethyl, hydroxy, methoxy or ethoxy, most preferably H;

R⁵ is H, lower alkyl, fluoro(lower)alkyl, hydroxy(lower) alkyl, alkylcarbonyl, alkylsulfonyl, aminosulfonyl, and acylaminosulfonyl, most preferably methyl.

The compounds of formula (1) can be prepared by processes described below and exemplified in Reaction Scheme 1 for the synthesis of a compound of the formula

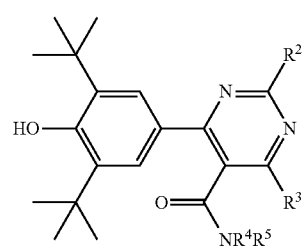

(1a)

wherein the substituents R² is methyl, R³=R⁴=H and R⁵ is methyl.

Reaction Scheme I

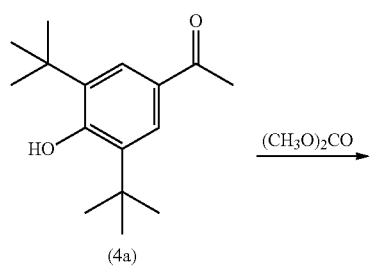

(4a)

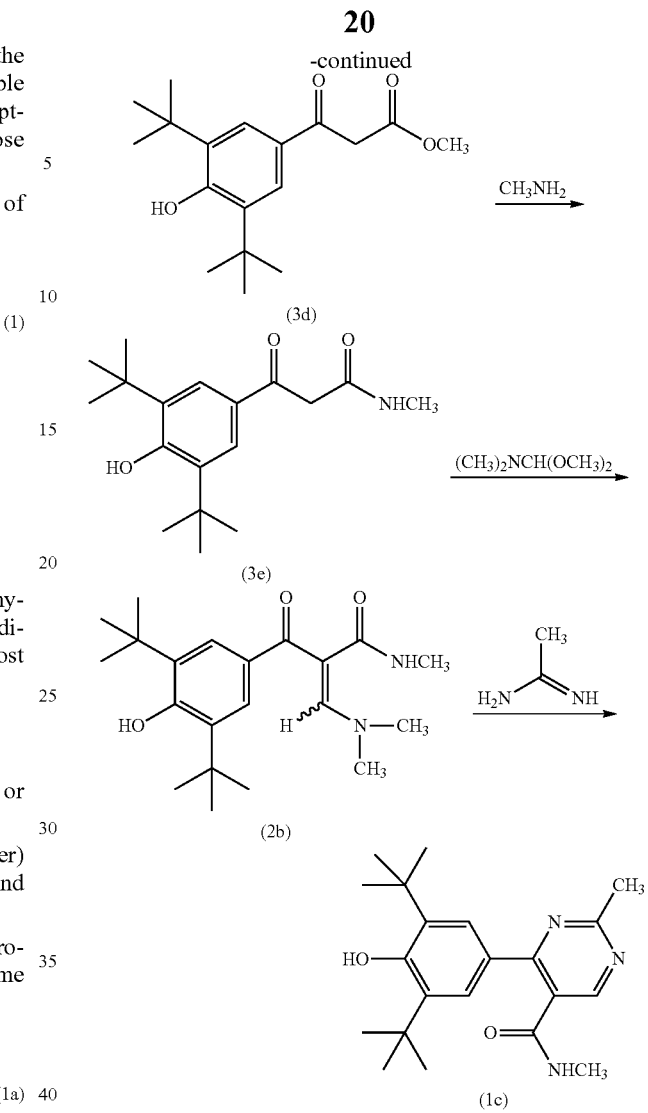

In Reaction Scheme I, the starting material of formula (4a) is known and can be prepared readily according to the published procedures. A compound of formula (3d) is prepared in analogy with a published procedure (Cushman, M., et al., J Med Chem 1991, 34, 798) by double-deprotonation of a compound of formula (4a) with a strong base such a lithium bis(trimethylsilyl)amide followed by reaction with a methoxycarbonyl transfer agent, such as dimethyl carbonate, in the presence of a nonprotic solvent such as tetrahydrofuran at ca. 0° C. to −70° C., preferably at ca. −55° C., with subsequent warming to ca. 0° C. The resulting compound of formula (3d) is recovered, after acidification of the reaction mixture, preferably by extraction, concentration, and crystallization. The compound of formula (3d) is then treated with methylamine, most conveniently with a commercially available 40% methylamine solution in water, to give a compound of formula (3e) which is recovered, most conveniently by evaporation of the reaction mixture, and may be further purified by crystallization. The compound of formula (3e) is then condensed in an inert solvent, such as toluene at elevated temperature, preferably between ca. 50 and 110° C., with an N,N-dialkylformamide dialkyl acetal, such as N,N-dimethylformamide dimethyl acetal, to give a compound of formula (2b). The compound of formula (2b) is reacted with acetamindine hydrochloride in a polar solvent such as 2-propanol, together with a suitable base. The cyclocondensation is brought to completion at elevated temperature, preferably at around 80° C., within ca. 4 h. The resulting compound of formula (1c) is recovered, for example by extraction, chromatography and crystallization.

The compounds of formula

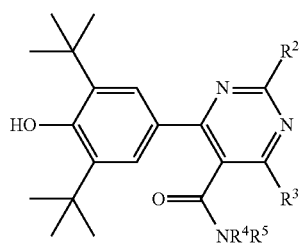

(1a)

wherein the substituents $R^2$ and $R^3$ are both methyl, $R^4$ is H and $R^5$ is methyl, can be prepared by a method as exemplified in Reaction Scheme II.

hydrochloride and a suitable base, followed by product recovery analogous to the one described above, gives a compound of formula (1d).

The compounds of the formula

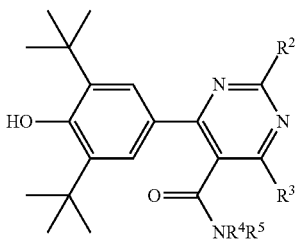

(1a)

wherein the substituents $R^2=R^5=$methyl, and $R^3=R^4=$H, can be prepared by a method as exemplified in Reaction Scheme III.

Reaction Scheme II

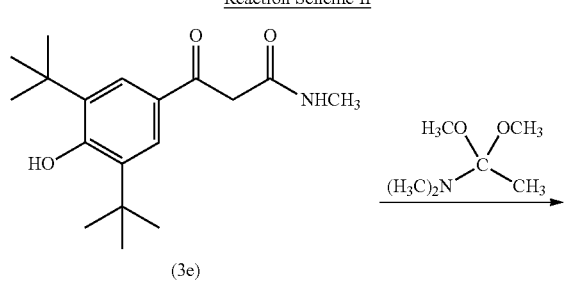

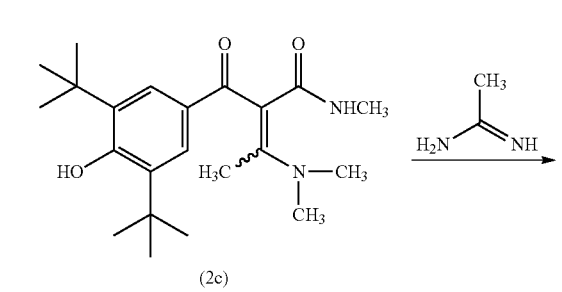

Reaction Scheme III

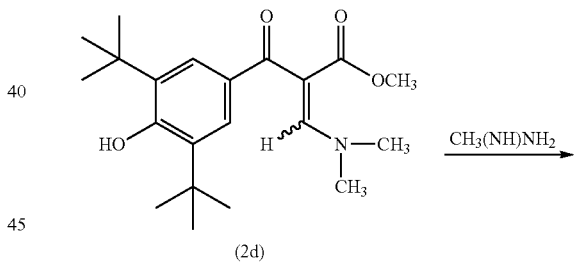

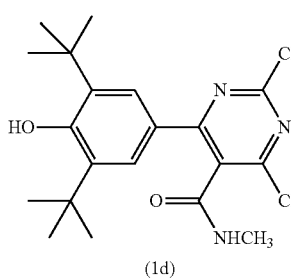

According to Reaction Scheme II, a compound of formula (3e) is reacted with N,N-dimethylacetamide dimethylacetal as described in connection with Reaction Scheme 1. This process gives a compound of formula (2c) as a mixture of geometric isomers. A following treatment with acetamidine

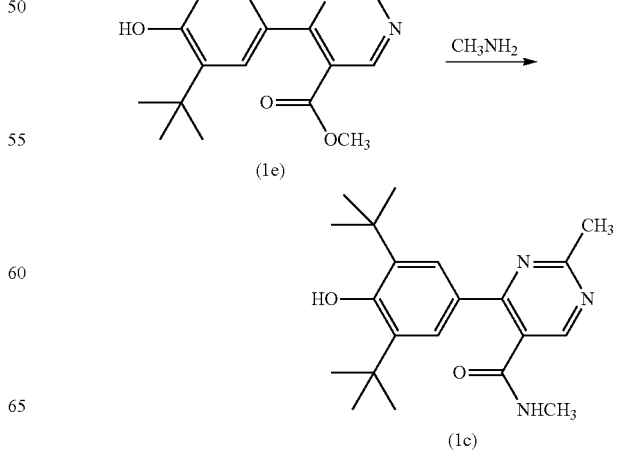

In Reaction Scheme III, the starting material of formula (3d) is prepared as described above and shown in Reaction Scheme I. It will also be appreciated that the entire side chain of the formula C(O)CH$_2$C(O)OR, as present in compound of formula (3d), can also be introduced by different methods, for example by the reaction of the known 4-hydroxy-3,5-ditert-butyl benzoyl chloride, either with Meldrum's acid (Oikawa, Y, et al., Org Syn 1990, Coll Vol VII, 359), or with potassium ethyl malonate using a magnesium chloride-triethylamine base system in either acetonitrile or ethyl acetate solvents (Clay, R J, et al., Synthesis 1993, 290). The compound of formula (3d) is then condensed in an inert solvent such as toluene at elevated temperature, preferably between 50 and 110° C., with an N,N-dialkylformamide dialkyl acetal such as N,N-dimethylformamide dimethyl acetal, to give a compound of formula (2d). Said compound is reacted with acetamidine hydrochloride in a polar solvent such as 2-propanol, together with a suitable base as described previously in Reaction Scheme I. The cyclocondensation is brought to completion at elevated temperature, preferably at around 80° C., within ca. 4 h. A resulting compound of formula (1e) is recovered, for example by extraction, chromatography and crystallization. An aminolysis of a compound of formula (1e) most conveniently with a commercially available 40% methylamine solution in water, or with a solution of the anhydrous methylamine gas in an inert solvent such as dioxane or tetrahydrofuran contained in a pressure vessel, preferably at temperature of about 30 to 90° C., gives a compound of formula (1c) which is recovered by evaporation of the solvent followed by chromatography and crystallization.

The compounds of formula

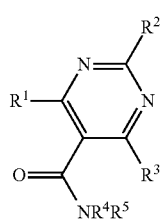

(1)

wherein the substituents R$^1$, R$^2$, R$^3$, R$^4$, and R$^5$ are as described above, can also be prepared by processes described below and exemplified in Reaction Scheme IV.

Reaction Scheme IV

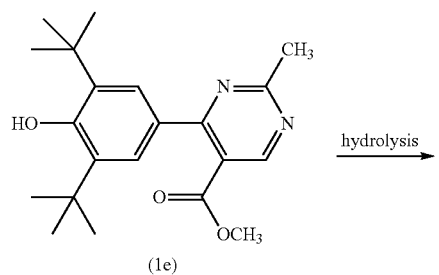

According to Reaction Scheme IV, the starting material of formula (1e), prepared as described previously and illustrated in Scheme III, is hydrolyzed under conventional saponification conditions using a slight excess of a suitable inorganic base such as sodium hydroxide. Upon acidification, an aqueous suspension of a compound of the formula (10 results. Said compound is recovered by filtration, and then purified, for example by recrystallization. A compound of the formula (1g) is prepared by coupling a compound of formula (10 with an amine component of formula HNR$^4$R$^5$. The condensation is under conventional peptide synthesis conditions, using an activating agent for the carboxyl group, for example benzotriazol-1-yloxytris-(dimethylamino)phosphonium hexafluorophosphate (BOP reagent), together with one equivalent of a compound of the formula HNR$^4$R$^5$ and one equivalent of a tertiary amine such as N,N-diisopropylethylamine. If the compound of the formula HNR$^4$R$^5$ exists in the form of a salt, then 2 equivalents of the tertiary amine are used. A resulting compound of formula (1g) is recovered, for example by neutralization and addition of water, and then purified, for example by crystallization.

The compounds of formula

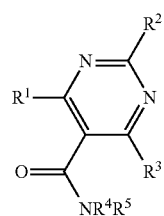

(1)

wherein the substituents R$^1$, R$^2$, R$^3$, R$^4$, and R$^5$ are as described above, can also be prepared by processes described below and exemplified in Reaction Scheme V.

Reaction Scheme V

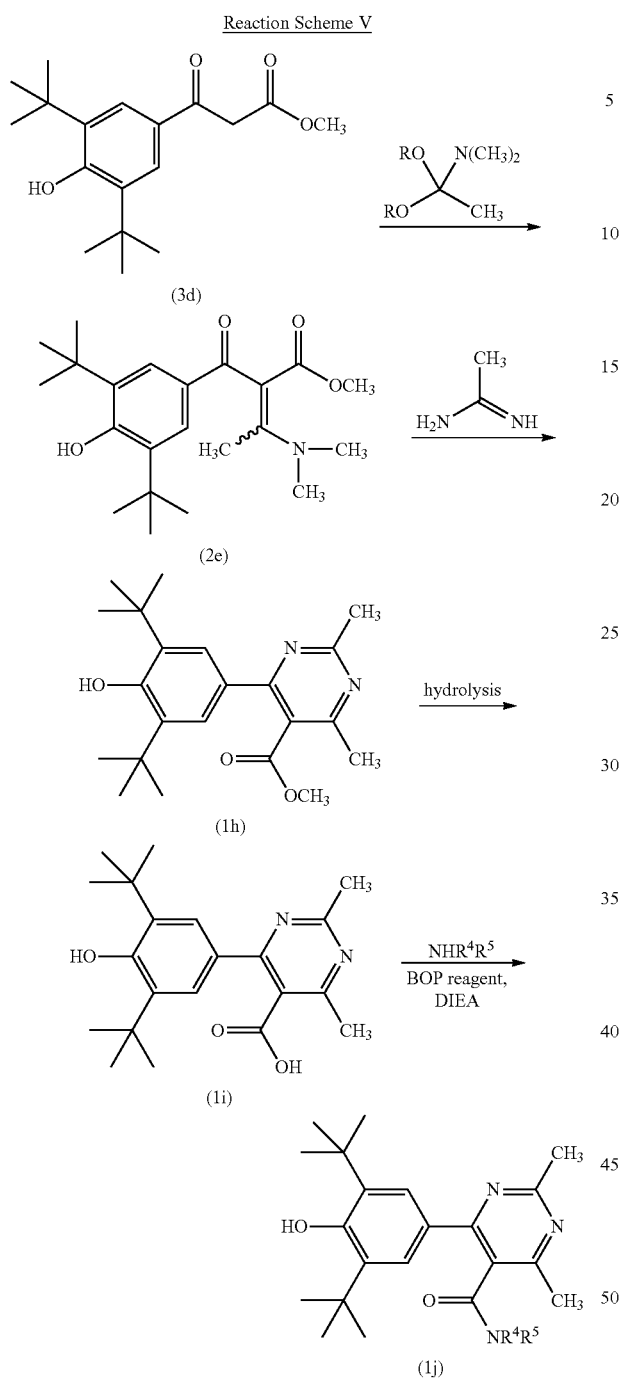

Reaction Scheme VI

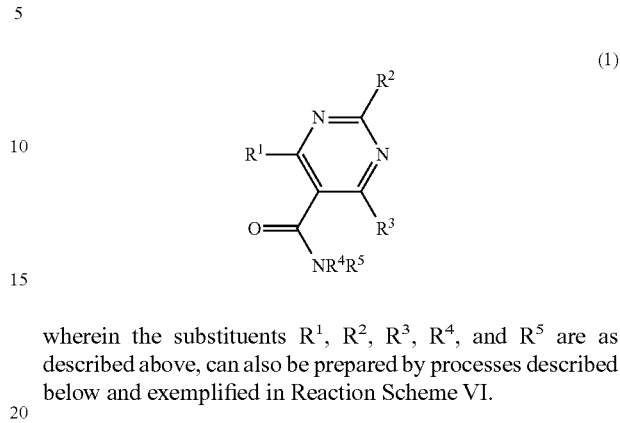

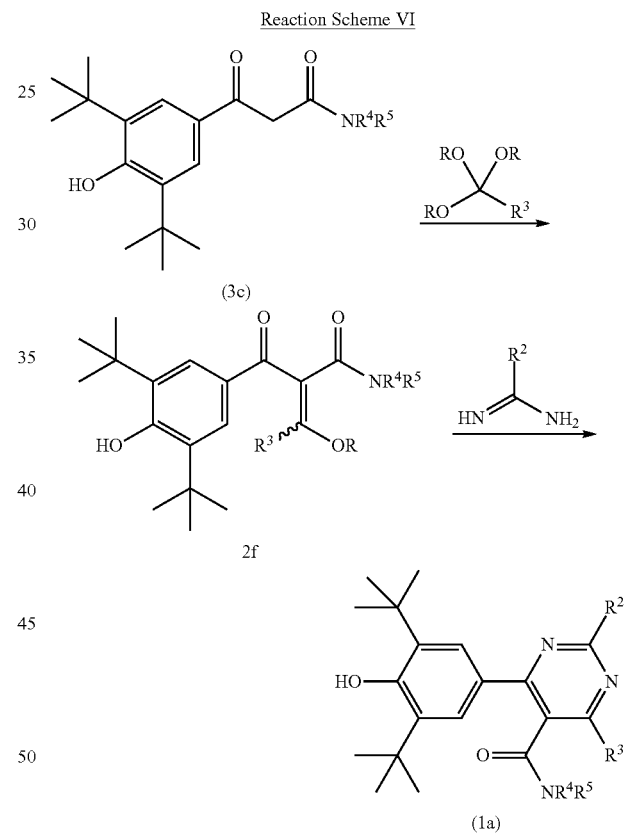

to those skilled in the art, and also exemplified previously in Scheme IV, to make a carboxamide of the formula (1j).

The compounds of formula $$(1)$$

wherein the substituents $R^1$, $R^2$, $R^3$, $R^4$, and $R^5$ are as described above, can also be prepared by processes described below and exemplified in Reaction Scheme VI.

According to Reaction Scheme V, the starting material is prepared by reacting a compound of the formula (3d) with N,N-dimethylacetamide dimethyl acetal to furnish a compound of formula (2e). This process, and the subsequent cyclocondensation with acetamidine shown in the Reaction Scheme above, is conducted in a fashion analogous to the one described previously and illustrated in Reaction Scheme III. The resulting compound of the formula (1h) is saponified as described previously and illustrated in Reaction Scheme IV. The free carboxylic acid function in the resulting compound of formula (1i) is coupled with an amine component of the formula $HNR^5R^6$ using peptide formation technology known According to Reaction Scheme VI, a compound of the formula (3c), wherein the substituent $NR^4R^5$ is as defined above, is reacted with a donor of an acyl equivalent such as a trialkyl orthoalkanoate, for example trimethyl orthoformate, triethyl orthoformate, trimethyl orthoacetate, and the like, under conditions mentioned previously. The resulting compound of the formula (20, wherein the substituents $R^4$ and $R^5$ are as defined above and $R^3$ is H or a lower alkyl, is then subjected to a cyclocondensation with formamidine or an amidine derivative, in a fashion analogous to those described previously and illustrated in Reaction Schemes I, II, and III, to produce a compound of the formula (1a).

The compounds of formula

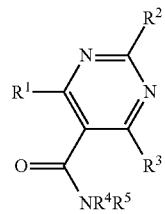

(1)

wherein the substituents R¹ is 5-hydroxy-4,6-di-tertbutyl-pyrimidin-2-yl and R², R³, R⁴, and R⁵ are as described above and previously designated as compound (1k), can also be prepared by processes described previously and exemplified in Reaction Scheme VII for the synthesis of the preferred compound of the formula (1m) shown below.

Reaction Scheme VII

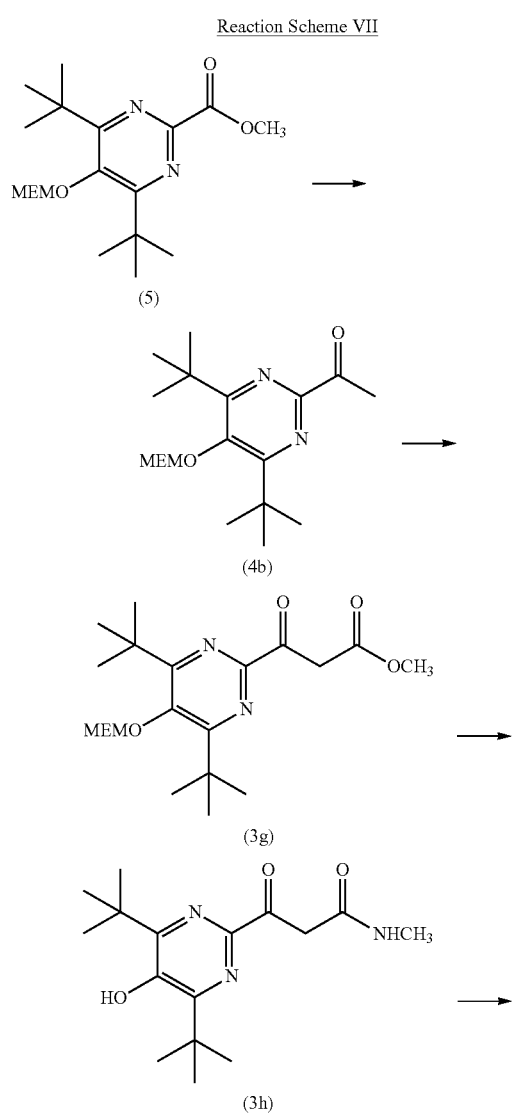

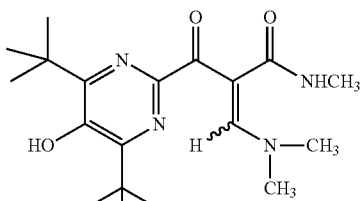

(2g)

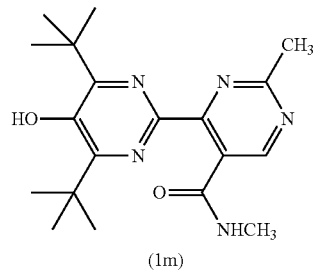

(1m)

According to Reaction Scheme VII, a compound of the formula (5), and described in the previously quoted U.S. Pat. No. 5,356,898, and wherein MEM stands for methoxyethoxymethyl, can be converted to the ketone of the formula (4b) by methods exemplified previously, of which the use of methylmagnesium chloride in the presence of hexamethylphosphoramide (Tetrahedron 1973, 29, 479-485) is preferred. The subsequent chain extension can be conducted in analogy with Example 1. Thanks to the MEM protective group in (4b), the excess of lithium bis(trimethylsilyl)amide can be reduced. The protective group is then removed after the chain extension by any of the known procedures; of those the original method using zinc bromide or titanium tetrachloride in dichloromethane (Corey, E J, et al., Tetrahedron Lett, 1976, 809) is preferred. The subsequent amination proceeds in analogy to Example 2. The resulting compound of the formula (3h) is converted to (2g) in analogy to Example 3, and the cyclocondensation of (2g) with acetamidine is conducted in analogy with Example 6 to furnish the compound of the formula (1m).

Especially preferred compounds of formula (1) are:
4-(3,5-ditert-butyl-4-hydroxy-phenyl)-N,2-dimethyl-pyrimidine-5-carboxamide;
4-(3,5-ditert-butyl-4-hydroxy-phenyl)-N-ethyl-2-methyl-pyrimidine-5-carboxamide;
4-(3,5-ditert-butyl-4-hydroxy-phenyl)-2-methoxy-N-methyl-pyrimidine-5-carboxamide;
4-(3,5-ditert-butyl-4-hydroxy-phenyl)-N,2,6-trimethyl-pyrimidine-5-carboxamide;
4-(3,5-ditert-butyl-4-hydroxy-phenyl)-N-hydroxy-N,2-dimethyl-pyrimidine-5-carboxamide;
4-(4,6-ditert-butyl-5-hydroxy-pyrimidin-2-yl)-N,2-dimethyl-pyrimidine-5-carboxamide;
4-(4,6-ditert-butyl-5-hydroxy-pyrimidin-2-yl)-N-ethyl-2-methyl-pyrimidine-5-carboxamide;
4-(4,6-ditert-butyl-5-hydroxy-pyrimidin-2-yl)-2-methoxy-N-methyl-pyrimidine-5-carboxamide;
4-(4,6-ditert-butyl-5-hydroxy-pyrimidin-2-yl)-2-dimethylamino-N-methyl-pyrimidine-5-carboxamide; and
4-(4,6-ditert-butyl-5-hydroxy-pyrimidin-2-yl)-N-hydroxy-N,2-dimethyl-pyrimidine-5-carboxamide.

As mentioned earlier, the compounds of formula (1) and pharmaceutically acceptable salts of compounds of formula (1) are useful in the treatment or prevention of inflammations and diseases where inflammation is the innate cause. For example, they can be used as anti-inflammatory agents in the treatment of inflammatory joint diseases, such as arthritis. To substantiate this assertion, representative compounds of formula (1) were tested for their inflammation-inhibiting properties in the adjuvant-induced arthritis test in rats as described in Int J Immunopharma, 1900, 12, 709-712.

A quantity of 0.1 ml of a 0.5% (weight/volume) suspension of heat-killed and dried mycobacterium butyricum in heavy mineral oil, containing 0.2% digitonin, is injected into the base of the tail of male Lewis rats (120-140 g). The animals are housed individually and receive feed and water ad libitum. The thus-induced arthritis is allowed to develop without treatment during 21 days. On day 21 the body weight of each animal is determined. At the same time, the volumes of the two hind paws of each animal are measured by immersing the paws in an aqueous plethysmograph up to the height of the lateral malleolus. Thereupon, the animals are divided into groups, each group comprising six animals of approximately the same average volumes of the hind paws. One group is administered suspending vehicle. The other groups are administered the micronized test compound suspended in an aqueous suspending vehicle [0.9% NaCl (w/v) containing 0.5% carboxymethyl cellulose (w/v), 0.86% benzyl alcohol (v/v) and 0.39% Tween 80 (v/v)]. The test compound in aqueous suspending vehicle (or vehicle alone) is administered to the animals by intubation each day over a period of seven days. The effect of the test compounds is monitored daily by measurement of the hind paw volumes and body weights. At the end of the treatment period (day 28), body weights and volumes of the hind paws are again determined. The changes over the treatment period are calculated. The change in paw volume or body weight equals the paw volume or body weight on day 28 minus paw volume or body weight on day 21.

The results determined for representative compounds of formula (1) in the test described hereinbefore are set forth in the following Table I. Therein, the results for vehicle is in parenthesis following the results for each tested compound at a dose level of 30 mg/kg in each test.

TABLE I

| | Inflammation-inhibiting Activity | | |
|---|---|---|---|
| Compound | Left paw volume (mL) | Right paw volume (mL) | Body weight change (g) |
| A | −0.88 ± 0.12 (0.09) | −0.99 ± 0.15 (0.08) | 25 ± 3 (13) |
| B | −0.68 ± 0.09 (0.06) | −0.47 ± 0.04 (0.09) | 16 ± 1 (10) |
| C | −0.65 ± 0.02 (0.09) | −0.61 ± 0.01 (0.08) | 28 ± 2 (13) |

A: 4-(3,5-ditert-butyl-4-hydroxy-phenyl)-N,2-dimethyl-pyrimidine-5-carboxamide (1c);
B: 4-(3,5-ditert-butyl-4-hydroxy-phenyl)-N,2,6-trimethyl-pyrimidine-5-arboxamide;
C: 4-(3,5-ditert-butyl-4-hydroxy-phenyl)-2-methox-N-methyl-pyrimidine-5-carboxamide.

The compounds of formula (1), and salts thereof, can be used as medicaments, for example, in the form of pharmaceutical preparations. The pharmaceutical preparations can be administered orally, for example, in the form of tablets, coated tablets, dragees, hard and soft gelatin capsules, solutions, emulsions or suspensions, and the administration can also be effected rectally, for example, in the form of suppositories, or parenterally, for example, in the form of solutions for injection.

The dosage can vary within wide limits and will, of course, be adjusted to the individual requirements in each particular case. The compounds of formula (1) can be administered at a daily dosage of about 1 mg/kg body weight to about 30 mg/kg body weight.

For the preparation of pharmaceutical dosage forms, the compounds of formula (1) and their pharmaceutically acceptable addition salts can be processed with pharmaceutically inert inorganic or organic carriers. Lactose, maize starch or related materials, talc, stearic acid or its salts, and the like, can be used, for example, as carriers for tablets, coated tablets, dragees and hard gelatin capsules. Suitable carriers for soft gelatin capsules are, for example, vegetable oils, waxes, fats, semi-solid and liquid polyols and the like. Suitable carriers for the preparation of solutions, emulsions, and syrups are, for example, water, polyols, saccharose, invert sugar, glucose and the like. Suitable carriers for injection solutions are, for example, water, alcohols, polyols, glycerol, vegetable oils and the like. Suitable carriers for suppositories are, for example, natural or hardened oils, waxes, fats, semi-liquid or liquid polyols and the like, The pharmaceutical preparations can also contain preserving agents, solubilizers, stabilizing agents, wetting agents, emulsifying agents, sweetening agents, coloring agents, flavoring agents, salts for varying the osmotic pressure, buffers, coating agents or antioxidants. In addition, they can also contain other therapeutically valuable substances.

The examples which follow further illustrate the embodiment.

EXAMPLE 1

Methyl 3-(3,5-ditert-butyl-4-hydroxy-phenyl)-3-oxo-propanoate

A 1-L 3-neck flask was charged with tetrahydrofuran (133 g) and a 1 M solution of lithium bis(trimethylsilyl)amide in tetrahydrofuran (250 mL) was added. The solution was stirred and cooled to −50 to −60° C. and a solution of 3,5-ditert-butyl-4-hydroxyacetophenone (19.4 g) dissolved in tetrahydrofuran (total volume of 165 mL) was added within 30 minutes at a temperature at or below −55° C. The mixture was stirred for 15 min, and then allowed to warm to −20° C. by removing the cooling bath and dimethyl carbonate (10 mL) was added in a slow stream. As soon as the carbonate addition was complete the mixture was allowed to reached a temperature of −5° C. and was then immersed into an ice bath and stirred for a period of 30 minutes or until TLC indicated complete reaction. At that time the staring material was no longer detectable. The conversion of the starting material (Rf 0.64) to the title compound (Rf 0.52) was monitored by TLC using 1:4 ethyl acetate-hexane as solvent and UV detection of the substances. Stirring was continued for an additional 30 minutes and the mixture was poured into a flask containing ice (218 g) and a 1 M sulfuric acid solution (300 mL). The mixture was equilibrated and extracted with ethyl acetate (300 mL) then re-extracted with an additional portion of ethyl acetate (100 mL). The combined extracts were washed three times with water (150 mL each) then with brine (75 mL). The resulting ethyl acetate solution was evaporated and the residual orange oil was taken up in cyclohexane and the solution concentrated to remove residual ethyl acetate, then diluted with hexane and allowed to crystallize. The mother liquor was decanted and the crystals rinsed with hexane and dried to give the title compound (20.81 g). The mother liquor was concentrated to a syrup, diluted with little pentane then allowed to crystallize to afford additional product (2.70 g). This second crop was purified by chromatography on silica gel using 1:4 ethyl acetate-hexane as solvent. This material was added to the first crop to afford 22.8 g of the title compound (94.9% yield); TLC (1:4 ethyl acetate-hexane) Rf 0.52;

¹H-NMR (300 MHz, DMSO-d₆) δ 1.39 (9H, s), 3.61 (3H, s), 4.10 (2H, s), 7.70 (2H, s), 7.96 (1H, s).

EXAMPLE 2

3-(3,5-ditert-butyl-4-hydroxy-phenyl)-N-methyl-3-oxo-propanamide

A 500-mL flask was charged with methyl 3-(3,5-ditert-butyl-4-hydroxy-phenyl)-3-oxo-propanoate (24.3 g, 79.3 mmol) and a 40% methylamine solution (55 g). The solution was stirred for 2 h. The conversion of the starting material (Rf 0.91) to the title compound (Rf 0.4) was monitored by TLC using 1:1 ethyl acetate-hexane as solvent and UV detection of the substances. The solution was diluted with 2-propanol (100 mL) and evaporated. The solid residue was taken up in boiling 2-propanol (ca. 100 mL) and evaporated again. The residue was again taken up in boiling toluene (ca. 75 mL) and the hot solution was concentrated to afford a crystalline suspension. This suspension was re-dissolved by heating and the hot solution was diluted with cyclohexane (80 mL) to cause immediate crystallization. The suspension was homogenized by reheating, allowed to cool to room temperature, then refrigerated overnight and filtered. The filter cake washed with cyclohexane and hexane, dried to constant weight at 65° C. and 20 torr to afford 22.77 g of the title compound. This material was recrystallized by dissolving in boiling toluene (ca. 120 mL) followed by the addition of cyclohexane (100 mL). The suspension was allowed to cool to room temperature, then refrigerated and filtered. The filter cake was washed with cyclohexane then hexane and dried to constant weight at 65° C. and 20 ton to afford 22.03 g of the title compound (91%). TLC (1:1 ethyl acetate-hexane) Rf 0.48; ¹H-NMR (300 MHz, DMSO-d₆) δ 1.37 (9H, s), 2.57 (3H, d, J=4.6 Hz), 3.73 (2H s), 7.73 (2H, s), 7.85 (1H, s), 8.08 (1H, br s).

EXAMPLE 3

2-(3,5-ditert-butyl-4-hydroxy-benzoyl)-3-dimethylamino-N-methyl-prop-2-enamide

A 100-mL round bottom flask was charged with 3-(3,5-ditert-butyl-4-hydroxy-phenyl)-N-methyl-3-oxo-propanamide (3.05 mg, 10 mmol) and toluene (20 mL). The mixture was heated and to the resulting hot solution was added N,N-dimethylformamide dimethyl acetal (1.50 mL, 11.3 mmol) with evolution of methanol. The mixture was stirred for 5 h without further heating then evaporated to an oil that was taken up in ethyl acetate (50 mL). The resulting solution was washed with water (4×50 mL) then with brine (20 mL), dried with sodium sulfate and evaporated to an oil and then further dried to a solid foam that was kept under high vacuum to reach a constant weight, then ground to a fine powder to afford 3.55 g of the title compound (98%). TLC (ethyl acetate) Rf 0.09. This material, and especially the equivalent material derived from N,N-dimethylacetamidine dimethyl acetal, is readily hydrolyzed to the starting material. It is therefore advisable to use the condensation product directly and immediately after solvent removal.

EXAMPLE 4

4-(3,5-ditert-butyl-4-hydroxy-phenyl)-2-dimethylamino-N-methyl-pyrimidine-5-carboxamide A 50-mL round bottom flask was charged with 3-(3,5-ditert-butyl-4-hydroxy-phenyl)-3-oxo-propanoic acid methyl amide (2.69 g, 8.81 mmol) and toluene (18 mL). The mixture was warmed to give a solution, then N,N-dimethylformamide dimethyl acetal (1.46 mL, 11 mmol) was added while the solution was still hot. The mixture was stirred for 2.5 h then evaporated. The residue was taken up in 2-propanol (28 mL) and 1,1-dimethylguanidine sulfate (1.80 g, 6.6 mmol) was added. The mixture was stirred at room temperature and a 1 M solution of potassium tert-butoxide in tert-butanol (21 mL) was added and the mixture was immersed into a bath maintained at 80° C. and stirred for 4 hours then at 50° C. overnight. The mixture was allowed to cool to room temperature, and was equilibrated with ethyl acetate (80 mL) and water (60 mL). The organic layer was washed with water (2×25 mL), once with brine (20 mL) then dried with sodium sulfate and evaporated to a brown solid. This material was boiled in dichloromethane (200 mL) without dissolving all solids. The mixture was allowed to cool and was filtered. The brown filtrate was charged to a column of silica gel G (70-230 mesh) in dichloromethane and using 1:4, 1:2, 1:1 ethyl acetate-hexane and ethyl acetate as mobile phases. The product was eluted with ethyl acetate and crystallized partly in the receptacles. The appropriate fractions were evaporated and the residue dissolved in a boiling ethanol-acetone mixture. The solution was concentrated, the resulting suspension diluted with cyclohexane and refrigerated. The solids were washed with 1:2 ethyl acetate-hexane to leave the title compound as a white powder, 1.52 g, 44.9% yield. TLC (ethyl acetate) Rf 0.73, TLC (1:1 ethyl acetate-hexane) Rf 0.20; ¹H-NMR (300 MHz, DMSO-d₆) δ 1.38 (9H, s), 2.64 (3H, d, J=4.5 Hz), 3.15 (6H, s), 7.60 (2H, s), 8.15 (1H, br s), 8.22 (1H, s).

EXAMPLE 5

4-(3,5-ditert-butyl-4-hydroxy-phenyl)-2-methoxy-N-methyl-pyrimidine-5-carboxamide O-methylisourea hydrogensulfate (3.44 g, 20 mmol) was added to a solution of 2-(3,5-ditert-butyl-4-hydroxy-benzoyl)-3-dimethylamino-N-methyl-prop-2-enamide (3.55 g, 9.87 mmol) in 2-propanol (37.5 mL). The suspension was stirred at room temperature for 10 min then a 1 M solution of potassium tert-butoxide in tert-butanol (37.5 mL) was added and the mixture was immersed into a bath maintained at 80° C. and stirred for 4 hours. The reaction mixture was allowed to cool to ambient temperature and was then distributed between dichloromethane (150 mL) and water (75 mL). The organic layer was washed with water (2×50 mL), once with brine (10 mL), dried over magnesium sulfate and evaporated. The residue obtained was dissolved in dichloromethane and flash-chromatographed using DCM, 1:19, 1:9, and 1:3 ethyl acetate-dichloromethane, followed by ethyl acetate as mobile phases. Early fraction eluted 3-(3,5-ditert-butyl-4-hydroxy-phenyl)-3-oxo-propanoic acid methyl amide, which is the solvolysis product of the starting material; the title compound was eluted using 1:3 ethyl acetate-dichloromethane. The fractions containing the product were evaporated; the residue redissolved in hot DCM, diluted with cyclohexane then heated to remove some DCM and allowed to crystallize. The solids obtained were redissolved in ethyl acetate, the solution filtered, concentrated, diluted with cyclohexane and allowed to crystallize to give white crystals. The solids were filtered off, washed with cyclohexane and hexane, and dried to constant weight at 55° C. and 20 ton to afford 1.20 g of the title compound (32.7% yield). TLC (ethyl acetate), Rf 0.68, ¹H-NMR (300 MHz, DMSO-d₆) δ 1.40 (9H, s), 2.75 (3H, d, J=3.9 Hz), 3.98 (3H, s), 7.55 (1H, s), 7.69 (2H, s), 8.44 (1H br s), 8.49 (1H, s).

EXAMPLE 6

4-(3,5-ditert-butyl-4-hydroxy-phenyl)-N,2-dimethyl-pyrimidine-5-carboxamide

A 50-mL round bottom flask was charged with 3-(3,5-ditert-butyl-4-hydroxy-phenyl)-3-oxo-propanoic acid methyl amide (3.05 g, 10 mmol) and toluene (20 mL). The mixture was warmed to give a solution, then N,N-dimethyl-formamide dimethyl acetal (1.60 mL, 12 mmol) was added while the solution was still hot. The mixture was stirred for 2 h at room temperature and 30 min 75° C. To this solution was added acetamidine hydrochloride (1.8908 g, 20 mmol) and 2-propanol (50 mL), followed by potassium tert. butoxide (3.14 g, 28 mmol). The stirred mixture was immersed into a bath maintained at 74° C. and after 50 min the temperature of the heating bath was increased to 80° C. and maintained for 80 min. The mixture was allowed to cool to ambient temperature and was equilibrated with water (50 mL), a 1 M solution of potassium dihydrogen phosphate and ethyl acetate (100 mL). The aqueous layer was discarded and the organic layer was washed with water (2×25 mL), brine (25 mL), dried with sodium sulfate, concentrated to a crystalline suspension and heated again to dissolve some of the solids. The resulting suspension was further diluted with cyclohexane and allowed to crystallize. The crystals were washed with cyclohexane and pentane, and dried. The resulting material (2.94 g) was dissolved in a mixture of acetone and ethanol. The solution was filtered, the filtrate was concentrated to a crystalline suspension, then reheated and sufficient hot ethanol was added to give a solution. This solution was concentrated until turbid, and then allowed to crystallize first at room temperature then at 5° C. The solids were filtered off, washed with 1:1 ethyl acetate-hexane and hexane to afford 2.50 g of the title compound (70% yield). TLC (EtOAc) Rf 0.30; ¹H-NMR (300 MHz, DMSO-d₆) δ 1.39 (9H, s), 2.65 (3H, s), 2.71 (3H, d, J=4.5 Hz), 7.50 (1H, s), 7.83 (2H, s), 8.50 (1H, br s), 8.72 (1H, s).

EXAMPLE 7

4-(3,5-ditert-butyl-4-hydroxy-phenyl)-N-methyl-2-methylsulfanyl-pyrimidine-5-carboxamide A 200-mL round bottom flask was charged with 3-(3,5-ditert-butyl-4-hydroxy-phenyl)-3-oxo-propanoic acid methyl amide (3.05 g, 10 mmol) and toluene (20 mL). The mixture was warmed to give a solution, then N,N-dimethyl-formamide dimethyl acetal (1.60 mL, 12 mmol) was added while the solution was still hot. The mixture was stirred overnight at ambient temperature. TLC (EtOAc) indicated complete conversion to the 3-(3,5-ditert-butyl-4-hydroxy-phenyl)-3-oxo-2-[(dimethylamino)methylene]-propanoic acid methyl amide. The mixture was evaporated under reduced pressure and the residue was taken up in 2-propanol (50 mL). To the resulting brown solution was added S-methylisothiouronium sulfate (2.78 g, 10 mmol). The suspension was stirred for 10 min, potassium t-butoxide (4.21 g, 37.5 mmol) was added and stirring continued first at room temperature for 10 min and then in a bath maintained at 82° C. for 3 h. The mixture was further stirred overnight at ambient temperature followed by equilibration with water (100 mL) and ethyl acetate (125 mL). The organic layer was washed with a 1 M solution of potassium dihydrogen phosphate (30 mL) then with water (3×30 mL) and brine (25 mL) and then dried over sodium sulfate and concentrated. This concentrate was diluted with cyclohexane and concentrated again, further diluted with cyclohexane and refrigerated to furnish the crude product (3.1 g). This material was recrystallized by dissolving it in hot ethanol and diluting with a small amount of water. This process of recrystallization was repeated to furnish nearly colorless crystals, 1.5 g (38.7%); TLC (ethyl acetate) Rf 0.82; ¹H-NMR (300 MHz, DMSO-d₆) δ 1.39 (9H, s), 2.55 (3H, s), 2.69 (3H, d, J=4 Hz), 7.55 (1H, s), 7.68 (2H, s), 8.47 (1H, s), 8.50 (1H, br s).

EXAMPLE 8

Tablet Formulation

Tablets of the following compositions are prepared as described below:

| TABLET FORMULATION (Wet Granulation) | | | | | |
|---|---|---|---|---|---|
| Item | Ingredients | mg/tablet | | | |
| 1 | Compound 1c | 25 | 100 | 250 | 500 |
| 2 | Anhydrous Lactose | 83 | 35 | 19 | 38 |
| 3 | Croscarmellose Sodium | 6 | 8 | 16 | 32 |
| 4 | Povidone K30 | 5 | 6 | 12 | 24 |
| 5 | Magnesium Stearate | 1 | 1 | 3 | 6 |
| | Total Weight (mg) | 120 | 150 | 300 | 600 |

Compound 1c is 4-(3,5-ditert-butyl-4-hydroxy-phenyl)-N,2-dimethyl-pyrimidine-5-carboxamide Manufacturing Procedure:

Step 1: Mix Items 1, 2 and 3 in a suitable mixer for 15 minutes.

Step 2: Granulate the powder mix from Step 1 with 20% polyvinyl pyrrolidone K30 solution.

Step 3: Dry the granulation from Step 2 at 50° C.

Step 4: Pass the granulation from Step 3 through suitable milling equipment.

Step 5: Add the Item 5 to the milled granulation from Step 4 and mix for 3 minutes Step 6: Compress the granulation obtained from Step 5 in a suitable press.

EXAMPLE 9

Capsule Formulation

Capsules of the following compositions are prepared as described below:

| CAPSULE FORMULATION | | | | | |
|---|---|---|---|---|---|
| Item | Ingredients | mg/tablet | | | |
| 1 | Compound 1c | 25 | 100 | 250 | 500 |
| 2 | Hydrous Lactose | 123 | 148 | — | — |
| 3 | Corn Starch | 35 | 40 | 35 | 70 |
| 4 | Talc | 15 | 10 | 12 | 24 |
| 5 | Magnesium Stearate | 2 | 2 | 3 | 6 |
| | Total Weight (mg) | 120 | 300 | 300 | 600 |

Compound 1c is 4-(3,5-ditert-butyl-4-hydroxy-phenyl)-N,2-dimethyl-pyrimidine-5-carboxamide Manufacturing Procedure:
Step 1: Mix Items 1, 2 and 3 in a suitable mixer for 30 minutes.
Step 2: Add Items 4 and 5 and mix for 3 minutes
Step 3: Fill into suitable capsules.

INCORPORATION BY REFERENCE

Patents and publications cited throughout this application reflect the levels of understanding of those skilled in the art to which the embodiments pertain. Said patents and publications are expressly incorporated herein in their entireties by reference.

EQUIVALENTS

Those skilled in the art will recognize, or be able to ascertain, using no more than routine experimentation, many equivalents of the specific embodiments of the invention described herein. Such equivalents are intended to be encompassed by the following claims.

The invention claimed is:

1. A pyrimidine carboxamide derivative compound of formula

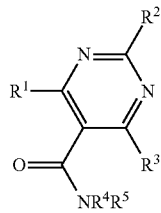

(1)

wherein
is 4,6-di-tert-butyl-5-hydroxypyrimidin-2-yl;
$R^2$ is H, alkyl, deuteroalkyl, carboxyalkyl, carboxy(amino)alkyl, aminoalkyl, aminocarbonylalkyl, haloalkyl, hydroxyalkyl, alkoxyalkyl, halo, thio, hydroxy, cyano, carboxy, carbamoyl, alkylsulfanyl, alkylsulfinyl, alkylsulfonyl, alkoxy, or amino;
$R^3$ is H, lower alkyl, deuteroalkyl, or halo(lower)alkyl;
$R^4$ is H, hydroxy, alkyl, deuteroalkyl, aminoalkyl, cyanoalkyl, haloalkyl, hydroxyalkyl, carboxyalkyl, alkoxyalkyl, lower alkoxy, deuteroalkoxy, or aryloxy;
$R^5$ is H, alkyl, deuteroalkyl, haloalkyl, hydroxyalkyl, alkoxycarbonylalkyl, aminocarbonylalkyl, aminosulfonylalkyl, carboxy(amino)alkyl, alkylcarbonylalkyl, alkylcarbonyl, arylcarbonyl, alkoxycarbonyl, alkylsulfonyl, or arylsulfonyl.

2. The compound according to claim 1, wherein
$R^2$ is lower alkyl, deutero(lower)alkyl, lower alkoxy, alkylsulfanyl, alkylsulfonyl, or amino;
$R^3$ is H, methyl, trideuteromethyl, or trifluoromethyl;
$R^4$ is H, hydroxy, lower alkyl, deutero(lower)alkyl, cyano(lower)alkyl, halo(lower)alkyl, hydroxy(lower)alkyl, carboxy(lower)alkyl, alkoxy(lower)alkyl, amino(lower)alkyl, lower alkoxy deutero(lower)alkoxy, or aryloxy;
$R^5$ is H, lower alkyl, deutero(lower)alkyl, halo(lower)alkyl, alkylcarbonyl(lower)alkyl, or hydroxyl(lower)alkyl.

3. The compound according to claim 2, wherein
$R^2$ is methyl, ethyl, methoxy, methylsulfanyl, or amino;
$R^3$ is H or methyl;
$R^4$ is H, hydroxy, methyl, trideuteromethyl, ethyl, hydroxymethyl, hydroxyethyl, methoxy, or ethoxy;
$R^5$ is H, methyl, hydroxymethyl, trideuteromethyl, ethyl, 2-fluoroethyl, 2,2,2-trifluoroethyl, 2-hydroxyethyl, or cyclopropyl.

4. The compound according to claim 3, wherein
$R^2$ is methyl, methoxy, or dimethylamino;
$R^4$ is H, methyl, ethyl, hydroxyethyl, hydroxy, or methoxy; and
$R^5$ is methyl.

5. The compound according to claim 4, selected from the group consisting of:
4-(4,6-ditert-butyl-5-hydroxy-pyrimidin-2-yl)-N,2-dimethyl-pyrimidine-5-carboxamide;
4-(4,6-ditert-butyl-5-hydroxy-pyrimidin-2-yl)-N-ethly-2-methyl-pyrimidine-5-carboxamide;
4-(4,6-ditert-butyl-5-hydroxy-pyrimidin-2-yl)-methoxy-N-methyl-pyrimidine-5-carboxamide;
4-(4,6-ditert-butyl-5-hydroxy-pyrimidin-2-yl)-dimethylamino-N-methyl-pyrimidine-5-carboxamide; and
4-(4,6-ditert-butyl-5-hydroxy-pyrimidin-2-yl)-N-hydroxy-N,2-dimethyl-pyrimidine-5-carboxamide.

6. The compound according to claim 5, wherein the pyrimidine carboxamide derivative compound is 4-(4,6-ditert-butyl-5-hydroxy-pyrimidin-2-yl)-N,2-dimethyl-pyrimidine-5-carboxamide.

7. A pharmaceutical composition containing a compound of the formula (1), selected from the group consisting of
4-(4,6-ditert-butyl-5-hydroxy-pyrimidin-2-yl)-N,2-dimethyl-pyrimidine-5-carboxamide;
4-(4,6-ditert-butyl-5-hydroxy-pyrimidin-2-yl)-N-ethyl-2-methyl-pyrimidine-5-carboxamide;
4-(4,6-ditert-butyl-5-hydroxy-pyrimidin-2-yl)-2-methoxy-N-methyl-pyrimidine-5-carboxamide;
4-(4,6-ditert-butyl-5-hydroxy-pyrimidin-2-yl)-2-dimethylamino-N-methyl-pyrimidine-5-carboxamide; and
4-(4,6-ditert-butyl-5-hydroxy-pyrimidin-2-yl)-N-hydroxy-N,2-dimethyl-pyrimidine-5-carboxamide, and containing an inert carrier.

8. The pharmaceutical composition of claim 7, wherein the compound of formula (1) is 4-(4,6-ditert-butyl-5-hydroxy-pyrimidin-2-yl)-N,2-dimethyl-pyrimidine-5-carboxamide.

* * * * *